US010709935B2

(12) United States Patent
Anderson

(10) Patent No.: US 10,709,935 B2
(45) Date of Patent: *Jul. 14, 2020

(54) SYSTEM AND METHOD FOR MEASURING AND ADJUSTING PHYSICAL RESISTANCE FOR ATHLETIC ACTIVITIES AND FITNESS EQUIPMENT

(71) Applicant: Intel Corporation, Santa Clara, CA (US)

(72) Inventor: Glen J. Anderson, Beaverton, OR (US)

(73) Assignee: Intel Corporation, Santa Clara, CA (US)

( * ) Notice: Subject to any disclaimer, the term of this patent is extended or adjusted under 35 U.S.C. 154(b) by 70 days.

This patent is subject to a terminal disclaimer.

(21) Appl. No.: 15/941,097

(22) Filed: Mar. 30, 2018

(65) Prior Publication Data

US 2018/0221714 A1 Aug. 9, 2018

Related U.S. Application Data

(63) Continuation of application No. 14/866,100, filed on Sep. 25, 2015, now Pat. No. 9,962,576, which is a (Continued)

(51) Int. Cl.
*A63B 24/00* (2006.01)
*A63B 69/16* (2006.01)
(Continued)

(52) U.S. Cl.
CPC ........ *A63B 24/0087* (2013.01); *A61B 5/1118* (2013.01); *A63B 24/0062* (2013.01); (Continued)

(58) Field of Classification Search
CPC ............ A63B 24/0087; A63B 24/0062; A63B 2024/0096
See application file for complete search history.

(56) References Cited

U.S. PATENT DOCUMENTS 5,218,865 A 6/1993 Djorup
6,450,922 B1 9/2002 Henderson et al.
(Continued)

FOREIGN PATENT DOCUMENTS

CN 1555758 12/2004
CN 103830884 6/2014
(Continued)

OTHER PUBLICATIONS

Chinese Patent Office, "First Office action," issued in connection with Chinese patent application No. 201680031441.5, dated Apr. 3, 2019, 6 pages. English Translation not available.
(Continued)

*Primary Examiner* — Megan Anderson
(74) *Attorney, Agent, or Firm* — Hanley, Flight and Zimmerman, LLC

(57) ABSTRACT

Methods, apparatus, systems and articles of manufacture for measuring and adjusting physical resistance for athletic activities and fitness equipment are disclosed. An example system includes a user-wearable sensor to measure a first level of physical effort during a first athletic activity using fitness equipment and to generate sensor data indicative of the measured first level of physical effort. The example system also includes a controller to receive the sensor data to perform a comparison of the sensor data and data from second athletic activity indicative of a second level of physical effort, and automatically generate a control signal to adjust a setting of the fitness equipment based on the comparison.

18 Claims, 11 Drawing Sheets

Related U.S. Application Data continuation-in-part of application No. 14/751,191, filed on Jun. 26, 2015, now Pat. No. 9,864,844.

(51) Int. Cl.

| | | |
|---|---|---|
| *A61B 5/11* | (2006.01) | |
| *G01S 19/19* | (2010.01) | |
| *G06F 1/16* | (2006.01) | |
| *A63B 69/06* | (2006.01) | |
| *G06F 3/01* | (2006.01) | |
| *G16H 20/30* | (2018.01) | |
| *A63B 22/06* | (2006.01) | |
| *A61B 5/01* | (2006.01) | |
| *A61B 5/024* | (2006.01) | |
| *A63B 71/06* | (2006.01) | |
| *A61B 5/00* | (2006.01) | |
| *A63B 22/00* | (2006.01) | |
| *A63B 22/02* | (2006.01) | |

(52) U.S. Cl.
CPC .......... *A63B 24/0075* (2013.01); *A63B 69/06* (2013.01); *A63B 69/16* (2013.01); *G01S 19/19* (2013.01); *G06F 1/163* (2013.01); *G06F 1/1626* (2013.01); *G06F 3/015* (2013.01); *G16H 20/30* (2018.01); *A61B 5/01* (2013.01); *A61B 5/024* (2013.01); *A61B 5/6806* (2013.01); *A61B 5/6807* (2013.01); *A61B 2503/10* (2013.01); *A61B 2562/0219* (2013.01); *A63B 22/0023* (2013.01); *A63B 22/0076* (2013.01); *A63B 22/02* (2013.01); *A63B 22/0605* (2013.01); *A63B 22/0664* (2013.01); *A63B 71/0622* (2013.01); *A63B 2024/0065* (2013.01); *A63B 2024/0068* (2013.01); *A63B 2024/0071* (2013.01); *A63B 2024/0081* (2013.01); *A63B 2024/0093* (2013.01); *A63B 2069/068* (2013.01); *A63B 2071/065* (2013.01); *A63B 2071/0661* (2013.01); *A63B 2071/0663* (2013.01); *A63B 2220/12* (2013.01); *A63B 2220/40* (2013.01); *A63B 2220/51* (2013.01); *A63B 2220/56* (2013.01); *A63B 2220/72* (2013.01); *A63B 2220/75* (2013.01); *A63B 2220/76* (2013.01); *A63B 2220/803* (2013.01); *A63B 2220/806* (2013.01); *A63B 2220/807* (2013.01); *A63B 2220/836* (2013.01); *A63B 2225/10* (2013.01); *A63B 2225/20* (2013.01); *A63B 2225/50* (2013.01); *A63B 2225/605* (2013.01); *A63B 2230/01* (2013.01); *A63B 2230/015* (2013.01); *A63B 2230/06* (2013.01); *A63B 2230/062* (2013.01); *A63B 2230/30* (2013.01); *A63B 2230/42* (2013.01); *A63B 2230/425* (2013.01); *A63B 2230/50* (2013.01); *A63B 2230/505* (2013.01); *A63B 2230/75* (2013.01); *A63B 2230/755* (2013.01)

(56) References Cited

U.S. PATENT DOCUMENTS

| | | | |
|---|---|---|---|
| 8,412,669 | B2 | 4/2013 | Bergeon et al. |
| 9,216,320 | B2 | 12/2015 | Ishii |
| 9,864,844 | B2 | 1/2018 | Durham et al. |
| 2008/0090703 | A1 | 4/2008 | Rosenberg |
| 2013/0165195 | A1 | 6/2013 | Watterson |
| 2013/0178334 | A1 | 7/2013 | Brammer |
| 2013/0274587 | A1 | 10/2013 | Coza et al. |
| 2014/0100678 | A1 | 4/2014 | Chapa, Jr. et al. |
| 2014/0135173 | A1 | 5/2014 | Watterson |
| 2014/0142459 | A1 | 5/2014 | Jayalth et al. |
| 2014/0280137 | A1 | 9/2014 | Anderson et al. |
| 2014/0379106 | A1 | 12/2014 | Weast et al. |
| 2015/0111698 | A1 | 4/2015 | Abbondanza et al. |
| 2015/0238817 | A1 | 8/2015 | Watterson et al. |
| 2016/0051858 | A1* | 2/2016 | Flaction .................. G09B 5/00 434/247 |
| 2016/0059076 | A1 | 3/2016 | Ishii |
| 2016/0129310 | A1 | 5/2016 | Ahmed et al. |
| 2016/0213980 | A1 | 7/2016 | Chen |
| 2016/0256745 | A1 | 9/2016 | Brammer |
| 2016/0271451 | A1* | 9/2016 | Wu .................... G06K 9/00342 |
| 2016/0375308 | A1 | 12/2016 | Anderson |

FOREIGN PATENT DOCUMENTS

| | | |
|---|---|---|
| TW | I371296 | 9/2012 |
| WO | 2014022438 | 2/2014 |

OTHER PUBLICATIONS

European Patent Office, "Extended European Search Report," issued in connection with European patent application No. 16814905.2, dated Jan. 18, 2019, 11 pages.

Taiwan Paten Office, "Office action," issued in connection with Taiwanese patent application No. 105114909, dated Jun. 26, 2019, 8 pages.

Germano, Beth, "Cambridge Company Creates Wheel That Turns Any Bicycle Into a Hybrid Electric," retrieved from [http://boston.cbslocal.com/2013/12/06/cambridge-company-creates-wheel-that-turns-any-bicycle-into-a-hybrid-electric/] on Dec. 6, 2013, CBS Boston, 1 page.

International Searching Authority, "Search Report," received for PCT Patent Application No. PCT/US2016/033033, dated Jul. 29, 2016, 5 pages.

International Searching Authority, "Written Opinion," received for PCT Patent Application No. PCT/US2016/033033, dated Jul. 29, 2016, 4 pages.

International Searching Authority, "International Preliminary Report on Patentability," issued in connection with PCT Application No. PCT/US2016/033033, dated Jan. 4, 2018, 6 pages.

United States Patent and Trademark Office, "Notice of Allowance," issued in connection with U.S. Appl. No. 14/751,191, dated May 10, 2017, 21 pages.

United States Patent and Trademark Office, "Notice of Allowance," issued in connection with U.S. Appl. No. 14/751,191, dated Sep. 13, 2017, 18 pages.

United States Patent and Trademark Office, "Non-Final Office Action," issued in connection with U.S. Appl. No. 14/751,191, dated Oct. 3, 2016, 13 pages.

United States Patent and Trademark Office, "Non-Final Office Action," issued in connection with U.S. Appl. No. 14/866,100, dated Apr. 19, 2017, 29 pages.

United States Patent and Trademark Office, "Notice of Allowance," issued in connection with U.S. Appl. No. 14/866,100, dated Aug. 24, 2017, 8 pages.

United States Patent and Trademark Office, "Notice of Allowance," issued in connection with U.S. Appl. No. 14/866,100, dated Sep. 25, 2017, 6 pages.

United States Patent and Trademark Office, "Notice of Allowance," issued in connection with U.S. Appl. No. 14/866,100, dated Jan. 24, 2018, 7 pages.

Wang, Yu-Hsiang et al., "A Microcantilever-based Gas Flow Sensor for Flow Rate and Direction Detection," CTIP of MEMS & MOEMS, Apr. 9-11, 2008, pp. 142-145, ISBN: 978-2-35500-006-5, EDA Publishing, (Abstract included), 3 pages.

United States Patent and Trademark Office, "Restriction Requirement," issued in connection with U.S. Appl. No. 14/866,100, dated Nov. 8, 2016, 5 pages.

European Patent Office, "Communication pursuant to Rules 70(2) and 70a(2) EPC," issued in connection with European patent application No. 16814905.2, dated Feb. 5, 2019, 1 pages.

(56) References Cited

OTHER PUBLICATIONS

Taiwan Paten Office, "Office action" issued in connection with Taiwanese patent application No. 105114909, dated Oct. 23, 2019, 2 pages. English translation not available.
Chinese Patent Office, "Notice of Grant," issued in connection with Chinese patent application No. 201680031441.5, dated Oct. 22, 2019, 4 pages.
Taiwan Patent Office, "Notice of Allowance" issued in connection with Taiwanese patent application No. 105114909, dated Feb. 12, 2020, 3 pages.

* cited by examiner

```
┌─────────────────────────────────────┐
│       Processing Logic for          │
│ Measuring and Adjusting Physical Resistance │
│ for Athletic Activities and Fitness Equipment │
│              -1100-                 │
└─────────────────────────────────────┘
                  ▼
┌─────────────────────────────────────┐
│ Measure a level of physical resistance in an athletic activity. │
│              -1110-                 │
└─────────────────────────────────────┘
                  ▼
┌─────────────────────────────────────┐
│ Generate sensor data indicative of the measured level of physical resistance. │
│              -1120-                 │
└─────────────────────────────────────┘
                  ▼
┌─────────────────────────────────────┐
│ Use the sensor data to determine if the measured level of physical resistance will achieve a desired performance level in the athletic activity. │
│              -1130-                 │
└─────────────────────────────────────┘
                  ▼
┌─────────────────────────────────────┐
│ Automatically generate control signals to adjust the level of physical resistance if the measured level of physical resistance is unlikely to achieve the desired performance level in the athletic activity. │
│              -1140-                 │
└─────────────────────────────────────┘
                  ▼
                ( End )
```

SYSTEM AND METHOD FOR MEASURING AND ADJUSTING PHYSICAL RESISTANCE FOR ATHLETIC ACTIVITIES AND FITNESS EQUIPMENT

RELATED APPLICATIONS

This patent arises as a continuation of U.S. patent application Ser. No. 14/866,100, which was filed on Sep. 25, 2015, and titled "System and Method for Measuring and Adjusting Physical Resistance for Athletic Activities and Fitness Equipment," which is a continuation-in-part of U.S. patent application Ser. No. 14/751,191, which was filed Jun. 26, 2015, and titled, "Wearable Device Normalization of Fitness Equipment Settings and Characteristics." U.S. patent application Ser. No. 14/866,100 and U.S. patent application Ser. No. 14/751,191 are hereby incorporated by reference herein in their entireties.

TECHNICAL FIELD

This patent application relates to electronic systems, mobile devices, wearable devices, fitness equipment, and computer-implemented software, according to various example embodiments, and more specifically to a system and method for measuring and adjusting physical resistance for athletic activities and fitness equipment.

BACKGROUND

Common fitness equipment (e.g., treadmills, bicycles, rowing machines, kayaks, etc.) can be used by a wide variety of individuals in many different environments. For example, a particular individual may exercise on one treadmill located in a home gym and subsequently exercise on another treadmill located in a hotel gym (e.g., while traveling), wherein the two treadmills may have different manufacturers, options and/or settings. Thus, the differences between the two treadmills may prevent the individual from being able to determine whether the fitness/workout sessions on the two treadmills are equivalent. Moreover, different individuals may be unable to compete with one another during fitness sessions due to the differences between their respective fitness equipment.

BRIEF DESCRIPTION OF THE DRAWINGS

The various embodiments are illustrated by way of example, and not by way of limitation, in the figures of the accompanying drawings in which:

FIG. 11 is a processing flow chart illustrating an example embodiment of a method as described herein.

DETAILED DESCRIPTION

Figure 1:
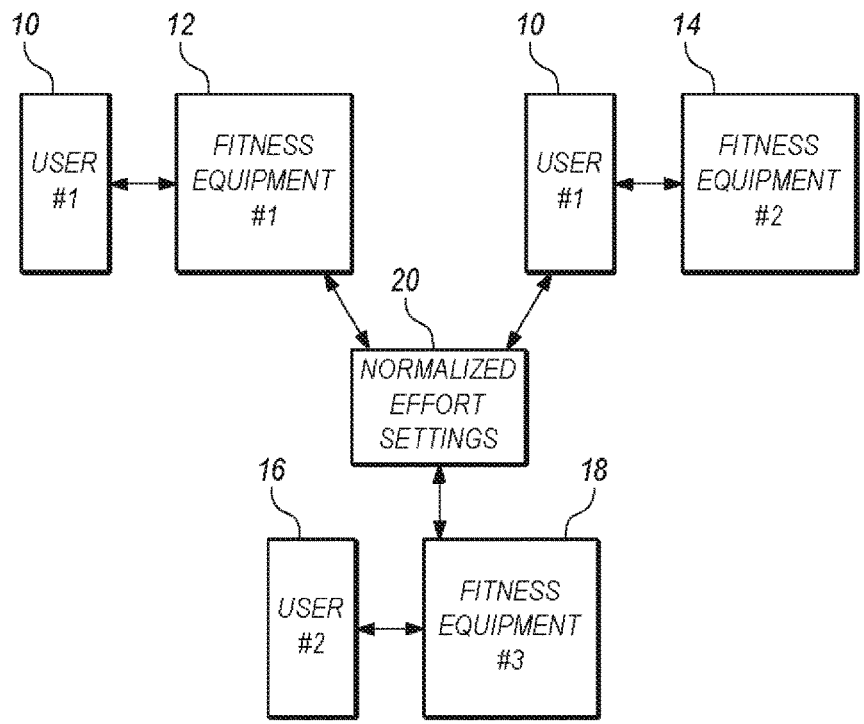
FIG. 1 is a block diagram of an example of an effort normalization according to an embodiment.

In the following description, for purposes of explanation, numerous specific details are set forth in order to provide a thorough understanding of the various embodiments. It will be evident, however, to one of ordinary skill in the art that the various embodiments may be practiced without these specific details.

In the various embodiments described herein, a system and method for measuring and adjusting physical resistance for athletic activities and fitness equipment are disclosed. Various types of athletic or fitness equipment are designed to reduce the effects of air resistance, water resistance, mechanical resistance, drag, or other types of physical resistance; because, such physical resistance is such an important variable in athletic performance. Headwinds can make biking and running, for example, much more difficult. For tracking performance, it can be helpful to measure the physical resistance and/or the level of physical effort needed to overcome this physical resistance as part of a workout or athletic activity to help the user automatically adjust a given athletic activity or performance relative to a required level of effort needed to overcome the wind resistance or other physical resistance. This is also true of tire pressure for mountain bike style wheels. In this case, tire pressure may vary, and it can help the user understand their performance, especially when tire pressure is low, which creates addition physical resistance and thus causes the rider to expend more effort. In some cases, maintaining low tire pressure (e.g., maintaining higher than normal levels of physical resistance) may be desirable for maximizing a workout for a given distance. Also, when two or more people of varying athletic ability work out together, it can be difficult for the stronger athlete (e.g., bicyclist) to get a good workout while remaining together with a weaker athlete. Automated adjustments in wheel resistance (e.g., through a mechanical mechanism) can allow the handicapping of a stronger bicycler to allow the stronger bicycler to have a good workout while riding with someone who is usually not as strong or fast.

One idea recognized and described herein is that physical resistance, especially wind/air resistance, water resistance, and wheel resistance, can be measured and adjusted during athletic activities. One goal is to allow normalization or equalization of performance levels across varying resistance conditions, and in some cases, to adjust physical resistance to make athletic or fitness performance more or less challenging (e.g., requiring a higher or lower level of effort). This normalization or equalization of performance levels allows people with different levels of fitness to work out effectively together or to give an individual a desired level of workout for a particular session.

The various embodiments described herein provide a system and method that can monitor performance, effort levels, and/or physical resistance levels in order to determine the effects of various physical resistance on athletic performance. The system and method can dynamically and automatically adjust physical resistance for athletic activities and/or fitness equipment to match the athletic performance or physical effort (e.g., velocity, timing, distance, calories burned, and/or other measures of athletic performance or physical effort) between users, including keeping users together on a course, such as a bicycle or kayaking course. As described in more detail below, a user-wearable sensor or a sensor installed or attached to fitness equipment can measure the physical resistance on a user's body or on the fitness equipment during an athletic activity, allowing a physical resistance variable to be taken into account when giving performance feedback to a user or when making automatic physical resistance adjustments. The disclosed system and method can also be used to normalize and compare athletic performance levels for one or more users across different days or other time periods or across different athletic events.

For example, as described in more detail below, a user-wearable device can measure air/wind resistance on a user's body during an athletic activity, allowing an air/wind resistance variable to be taken into account when giving performance feedback to a user or when making automatic physical resistance adjustments. Air/wind resistance on a user's body is directly proportional to the drag experienced by the rider. As such, air/wind resistance can be a measure of the physical resistance experienced by the bicycle and the rider. For another example, tire pressure on a bicycle can be measured by an attached or installed sensor on the bicycle during an activity, allowing a tire pressure variable to be taken into account when giving performance feedback or making automatic physical resistance adjustments. Tire pressure is inversely proportional to the level of friction experienced by the bicycle during the activity. As such, tire pressure can be a measure of the physical resistance experienced by the bicycle and the rider.

Once the level of physical resistance or effort for a particular athletic activity is measured using any of the techniques described above, the example embodiments can actively and automatically adjust the level of physical resistance for the particular athletic activity to match the athletic performance levels between multiple participants or for the same participant over multiple time periods. For example, bicycle wheel resistance (e.g., or other physical resistance) can be adjusted in various ways as described herein to allow users of varying abilities to be more closely matched during athletic activities. Adjustment can occur automatically, or the system can instruct the user on how to adjust the physical resistance level. Wheel resistance or assistance can be adjusted for the particular course or wind conditions. As described in more detail below, wheel resistance can be adjusted for increased resistance by variably applying a drag force (e.g., a brake) to the wheel. Wheel assistance can be adjusted for decreased resistance by variably applying a thrust force (e.g., engaging a motor) to the wheel. Concurrent monitoring of the physical resistance, effort required, or performance (e.g., velocity, timing, distance, calories burned, and/or other measures of athletic performance or physical effort) of multiple participants in an athletic activity can be used to match or even out the performance across the multiple participants in the activity. For example, if one participant gets a given distance ahead of other participants, the system of an example embodiment can increase that participant's resistance to allow the other participants to catch up. Alternatively, the system of an example embodiment can increase the thrust force for each of the other participants to enable them to catch up to the faster participant. In other embodiments, physical resistance adjustments can be automatically applied on fitness equipment used for weight training. In this example embodiment, the system can allow the effective weight being used by a lifter in a weight lifting activity to be adjusted during weight lifting repetitions (reps). For example, as the lifter gets tired, the physical resistance used during the weight lifting activity can be automatically reduced (e.g., the effective weight being lifted on a particular fitness machine can be automatically reduced) without the lifter having to stop to make adjustments. An example embodiment described herein also provides data sharing between users. Data sharing between users allows better profile ratings (and corresponding resistance levels relative to accompanying users) to be created by the system.

One advantage of the described example embodiments is that the example embodiments can provide automated physical resistance adjustments for athletic activities or fitness equipment (e.g., versus user adjustment) in real time. The embodiments with automatic physical resistance adjustment features can provide a more objective determination of settings and allow the user to ignore making such adjustments.

The various embodiments described herein include features for monitoring differences in athletic performance, effort levels, and/or physical resistance levels across a plurality of users who may be using different fitness equipment. Data related to these differences can be used by an example embodiment to normalize the data for better comparisons, based on analyzing force-to-motion ratios corresponding to the data received from user devices (e.g., wearables) and/or fitness equipment (e.g., bicycles, kayaks, weight lifting equipment, etc.). The various embodiments also include features for providing an adjustment prompt to advise the user to adjust a physical resistance level. The various embodiments described herein also include features for measuring physical resistance (e.g., wind resistance, water resistance, friction, drag, etc.) and/or automatically adjusting physical resistance to thereby adjust a level of effort required or to enable a desired performance level by a particular participant in a particular athletic activity. The example embodiments, in the case of measuring wind resistance for example, are not restricted to athletic activities with fitness equipment external to the user. For example, the example embodiments include user-worn sensors that can detect wind intensity and direction. As described in more detail below, the example embodiments can be implemented through existing hardware technologies, middleware, and new software (SW) components to coordinate the desired level of physical resistance.

As described in more detail below, the disclosed embodiments can be used with or integrated into a wide variety of electronic devices, such as mobile computing platforms, mobile devices, mobile systems, portable devices, wearables, desktop computing devices, portable computing devices, laptop computers, handheld computers, touch screen systems, and other electronic devices. In the various example embodiments, an electronic device may include a mobile system, which may refer to one or more of a laptop computer, a tablet computer, a wearable computer, or the like that may combine the functionality of a computing device with the usability/portability of a mobile device, tablet, a smartphone, a wearable device (such as a bracelet, ring, headset, etc.), or other mobile device. In some embodiments the mobile system may include more than one of the aforementioned devices, e.g., multiple devices that are coupled and that may create an improved user experience. The details of various example embodiments are provided below.

In various example embodiments, a physical resistance management (PRM) policy may be utilized to enhance an ability of a data processor in an electronic device to manage physical resistance settings based on a device context or usage preference. Device context may be determined through observation of platform states of components, sensors, and usage parameters. Various example embodiments are directed to contextual physical resistance management in athletic activities and fitness equipment using electronic devices such as mobile devices or systems. The details of various example embodiments are provided below in connection with the accompanying figures.

Turning now to FIG. 1, a fitness scenario is shown in which a first user 10 engages in a first fitness session (e.g., at time $t_0$) on first fitness equipment 12 such as, for example, a treadmill, elliptical trainer, weight machine, weight set, stationary bike, step machine, and so forth. The first fitness equipment 12 may generally have one or more settings that impact the amount of effort spent by the first user 10 during the first fitness session. For example, if the first fitness equipment 12 is a treadmill, the settings might include speed, incline, interval profile, etc. If, on the other hand, the first fitness equipment 12 is an elliptical trainer, the settings may include speed, resistance, interval profile, etc. The first user 10 may subsequently engage in a second fitness session (e.g., at time $t_1$) on second fitness equipment 14, wherein the second fitness equipment 14 may be the same type of equipment as the first fitness equipment 12 but originating from a different manufacturer or of a different model. For example, the first fitness equipment 12 may be a treadmill from Manufacturer #1 and the second fitness equipment 14 may be a treadmill from Manufacturer #2, the first fitness equipment 12 may be Model A of an elliptical trainer from Manufacturer #1 and the second fitness equipment 14 may be Model B of an elliptical trainer from Manufacturer #1, and so forth.

Accordingly, the second fitness equipment 14 may also have various settings that impact the amount of effort spent by the first user 10 during the second fitness session, wherein the settings of the second fitness equipment 14 differ from the settings of the first fitness equipment 12. For example, in the case of two different treadmills, the first fitness equipment 12 may have an incline setting that ranges from zero to ten and the second fitness equipment 14 may have an incline setting that ranges from zero to seven, wherein the degrees between each incline step may be different between the two treadmills. Similarly, in the case of two different elliptical trainers, the first fitness equipment 12 may have a resistance setting with a different range, minimum and/or maximum than the second fitness equipment 14.

Additionally, a second user 16 may engage in a third fitness session (e.g., at time $t_0$, $t_1$ or some other moment in time) on third fitness equipment 18, wherein the third fitness equipment 18 may be the same type of equipment as the first fitness equipment 12 and/or the second fitness equipment 14 but originating from a different manufacturer or of a different model. Accordingly, the third fitness equipment 18 may have one or more settings that differ from the settings of the second fitness equipment 14 and/or the settings of the first fitness equipment 12.

In the illustrated example, an effort normalization is conducted between the settings of the fitness equipment 12, 14, 18 in order to automatically generate normalized effort settings 20. The normalized effort settings 20 may enable the first user 10 to ensure that the amount of effort spent by the first user 10 during the second fitness session on the second fitness equipment 14 is equivalent to (or greater than) the amount of effort spent by the first user 10 during the first fitness session on the first fitness equipment 12. Moreover, the normalized effort settings 20 may enable the first user 10 and the second user 16 to compete with one another during the second fitness session on the second fitness equipment 14 and the third fitness session on the third fitness equipment, respectively. As will be discussed in greater detail, setting-specific user prompts may be generated to inform the users 10, 16 of the appropriate equipment settings to achieve the corresponding effort levels. Additionally, wearable sensor data may be used to conduct the effort normalization as well as generate the user prompts.

Figure 2A:
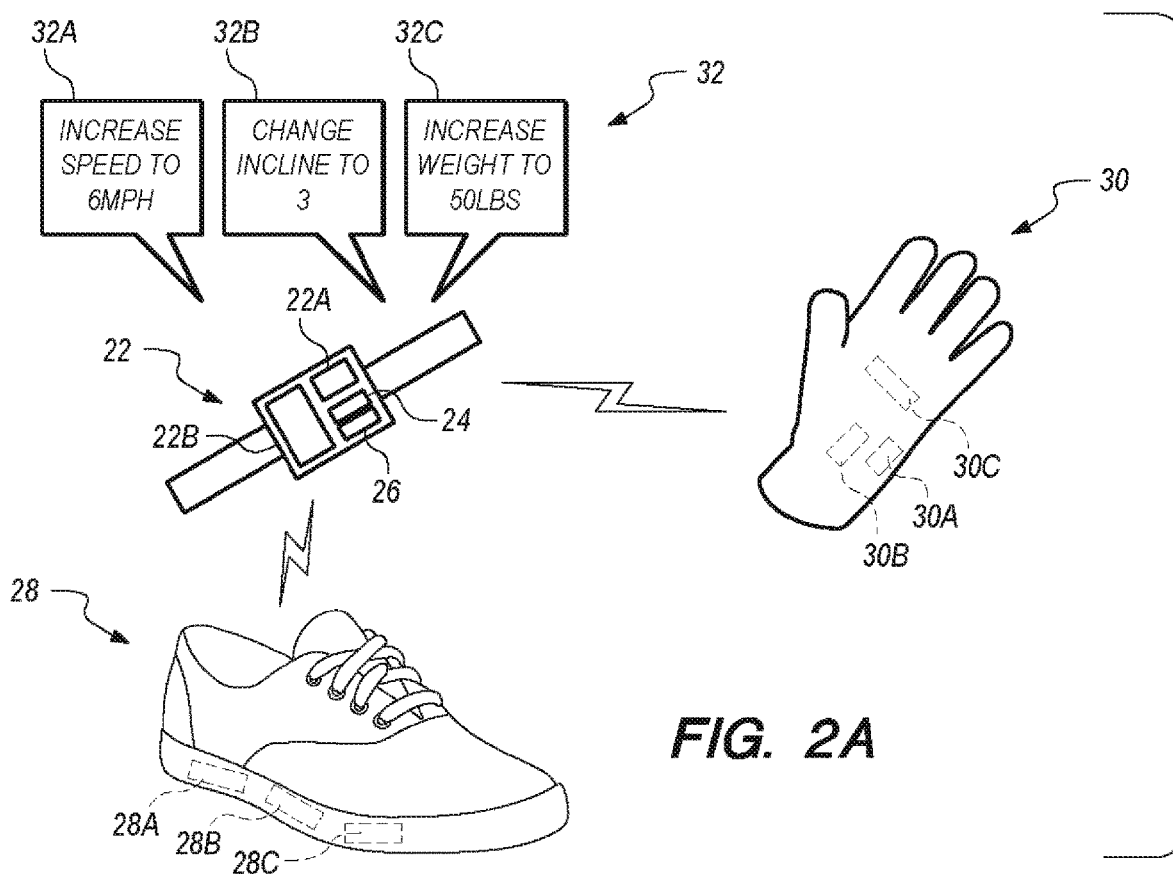
FIGS. 2A through 2C are illustrations of examples of wearable sensor data configurations according to embodiments.

FIG. 2A shows a wearable sensor data configuration in which a first wearable device 22 (22a-22b) having a housing with a wearable form factor (e.g., watch form factor in the example shown). The illustrated first wearable device 22 includes logic 22a (e.g., implemented in logic instructions, configurable logic, fixed-functionality logic hardware, etc., or any combination thereof) to obtain first wearable sensor data 24 associated with a first fitness session and first fitness equipment such as, for example, the first fitness equipment 12 (FIG. 1). The first wearable sensor data 24 may be obtained from, for example, a second wearable device 28 (28a-28c, e.g., a smart shoe/footwear) worn by the user (e.g., on the foot) and/or a third wearable device 30 (30a-30c, e.g., a smart glove) worn by the user (e.g., on the hand) during the first fitness session. For example, the second wearable device 28 might include a battery 28a to provide power to the second wearable device 28, a motion sensor 28b (e.g., accelerometer, gyroscope) to measure the physical movement of the second wearable device 28, and a force sensor 28c (e.g., piezoelectric sensor) to measure forces applied by the wearer of the second wearable device 28 to the fitness equipment, and so forth.

Accordingly, the amount of movement (e.g., gait in the case of a treadmill) as well as the amount of pressure applied through the bottom of the second wearable device 28 (e.g., to a foot pedal in the case of a stationary bike) during the first fitness session may be measured and communicated wirelessly to the first wearable device 22 as the first wearable sensor data 24. The second wearable device 28 may also be used during a second fitness session (e.g., if worn by the same user) to obtain second wearable sensor data 26 associated with a second fitness session and second fitness equipment such as, for example, the second fitness equipment 14 (FIG. 1). The first wearable device 22 may include memory to store the first wearable sensor data 24 and the second wearable sensor data 26.

As already noted, the first wearable sensor data 24 may also be obtained from the third wearable device 30 worn by the user (e.g., on the hand) during the first fitness session. For example, the third wearable device 30 may include a battery 30a to provide power to the third wearable device 30, a motion sensor 30b (e.g., accelerometer, gyroscope) to measure the physical movement of the third wearable device 30b, and a force sensor 30c (e.g., piezoelectric sensor) to measure forces applied by the wearer of the third wearable device 30 to the fitness equipment, and so forth.

Accordingly, the amount of movement (e.g., repetition stroke length in the case of a weight machine) as well as the amount of pressure applied through the palm of the third wearable device 30 (e.g., to a handle grip in the case of an elliptical trainer) during the first fitness session may be measured and communicated wirelessly to the first wearable device 22 as the first wearable sensor data 24. The third wearable device 30 may also be used during the second fitness session (e.g., if worn by the same user) to obtain the second wearable sensor data 26 associated with the second fitness session and the second fitness equipment. In addition, wearable devices such as, for example, the wearable devices 22, 28, 30, may be worn by another user such as, for example, the second user 16 (FIG. 1) in order to obtain third wearable sensor data during a third fitness session. The first and second wearable sensor data 24, 26 may also include other types of data relevant to effort such as, for example, perspiration sensor data, temperature sensor data, heart rate sensor data, etc.

In the illustrated example, the logic 22a of the first wearable device 22 conducts an effort normalization between one or more settings of the first fitness equipment, the second fitness equipment and/or the third fitness equipment, and generates one or more user prompts 32 (32a-32c) during the second fitness session via a user interface 22b (UI, e.g., display, speaker, haptic/vibration component) based on the effort normalization. For example, the user prompts 32 might include a speed adjustment prompt 32a (e.g., "Increase speed to 6 mph"), an incline adjustment prompt 32b (e.g., "Change incline to 3"), a resistance adjustment prompt 32c (e.g., "Increase weight to 50 lbs"), etc., or any combination thereof, wherein compliance with the user prompts 32 may generally ensure that the individual asserts a target amount of effort.

Figure 2B:
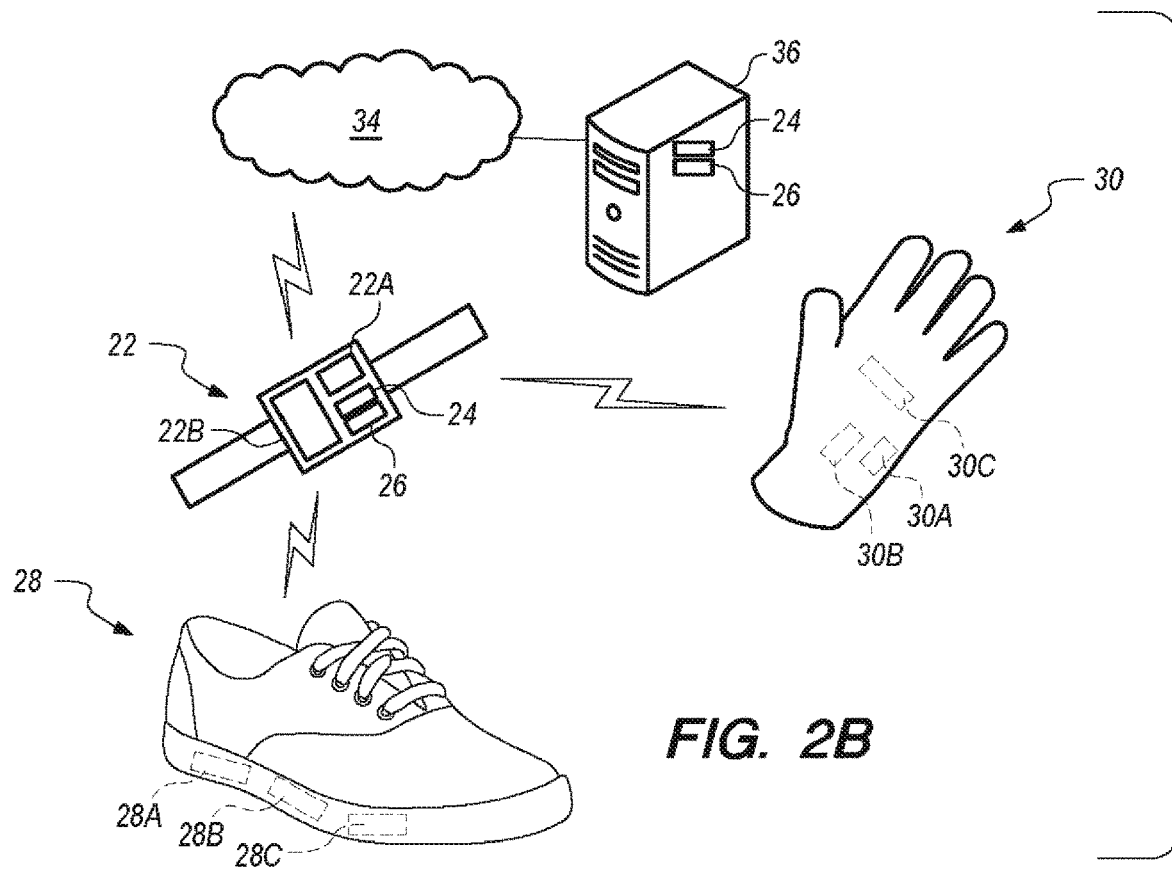
Figure 2C:
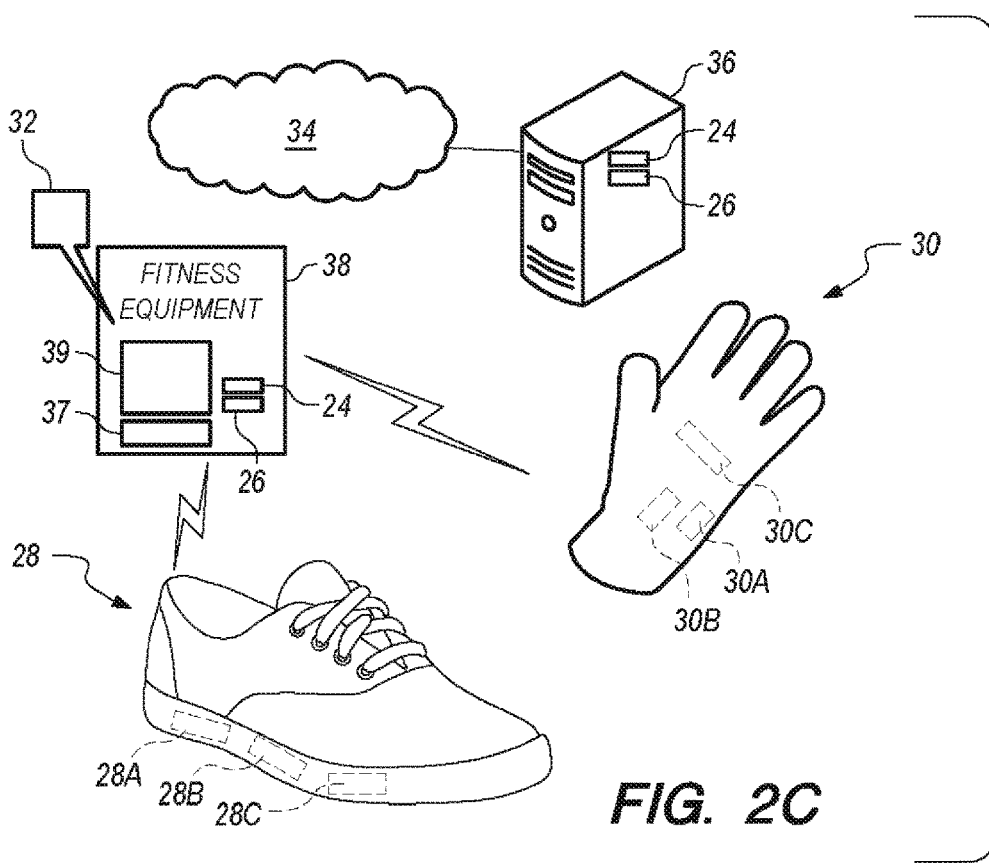

FIG. 2B demonstrates that the first wearable device 22 may also obtain the first wearable sensor data 24 and/or the second wearable sensor data 26 from a remote source such as a network 34 and/or a server 36. The illustrated solution may therefore be suitable in situations where, for example, the first and second wearable sensor data 24, 26 is associated with different users (e.g., who are competing with one another on their respective fitness equipment). The first wearable device 22 may also report locally obtained sensor data to the server 36. FIG. 2C demonstrates that fitness equipment 38 may include logic 37 to obtain the first and second wearable sensor data 24, 26, conduct the effort normalization and generate the user prompts 32 via a user interface 39 (e.g., display, speaker, haptic/vibration component).

Figure 3:
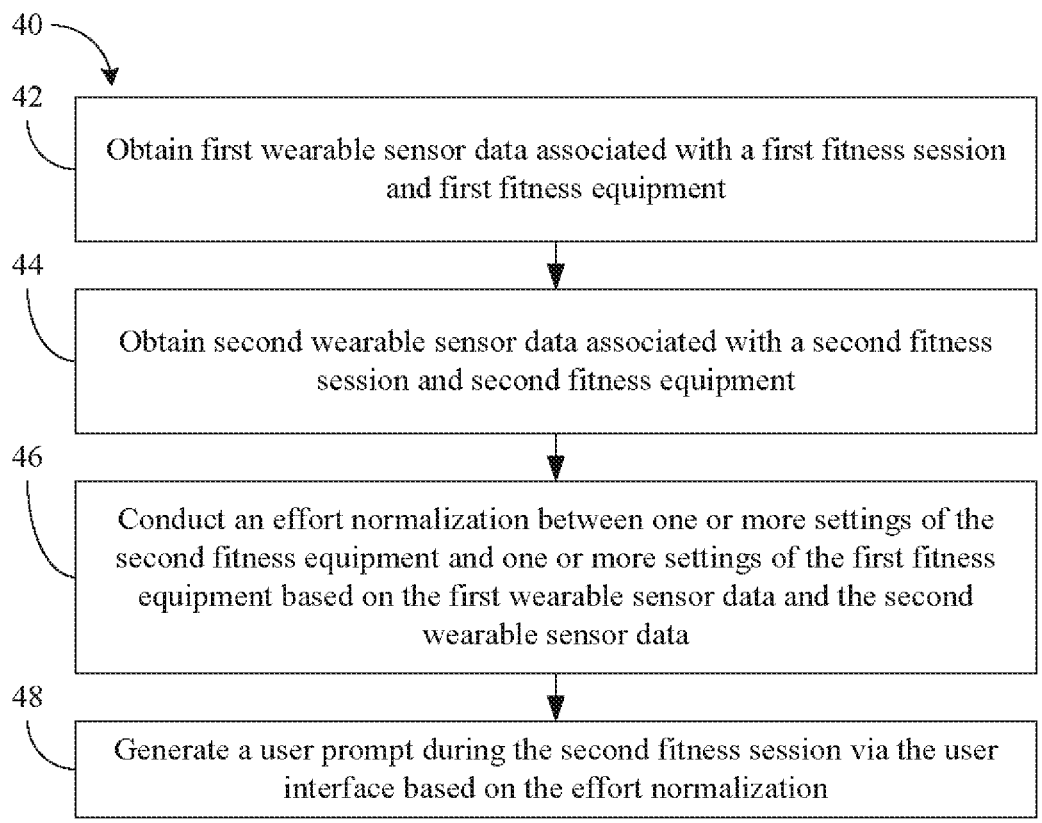
FIG. 3 is a flowchart of an example of a method of enhancing fitness sessions according to an embodiment.

FIG. 3 shows a method 40 of enhancing fitness sessions. The method 40 may generally be implemented in, for example, the first wearable device 22 (FIGS. 2A and 2B), the fitness equipment 12, 14 (FIG. 1), and/or the fitness equipment 38 (FIG. 2C), already discussed. More particularly, the method 40 may be implemented in one or more modules as a set of logic instructions stored in a machine- or computer-readable storage medium such as random access memory (RAM), read only memory (ROM), programmable ROM (PROM), firmware, flash memory, etc., in configurable logic such as, for example, programmable logic arrays (PLAs), field programmable gate arrays (FPGAs), complex programmable logic devices (CPLDs), in fixed-functionality logic hardware using circuit technology such as, for example, application specific integrated circuit (ASIC), complementary metal oxide semiconductor (CMOS) or transistor-transistor logic (TTL) technology, or any combination thereof.

Illustrated processing block 42 provides for obtaining first wearable sensor data associated with a first fitness session and first fitness equipment, wherein block 44 may obtain second wearable sensor data associated with a second fitness session and second fitness equipment. Additionally, illustrated block 46 conducts an effort normalization between one or more settings of the second fitness equipment and one or more settings of the first fitness equipment based on the first wearable sensor data and the second wearable sensor data. A user prompt may be generated at block 48 during the second fitness session via the user interface based on the effort normalization.

Figure 4:
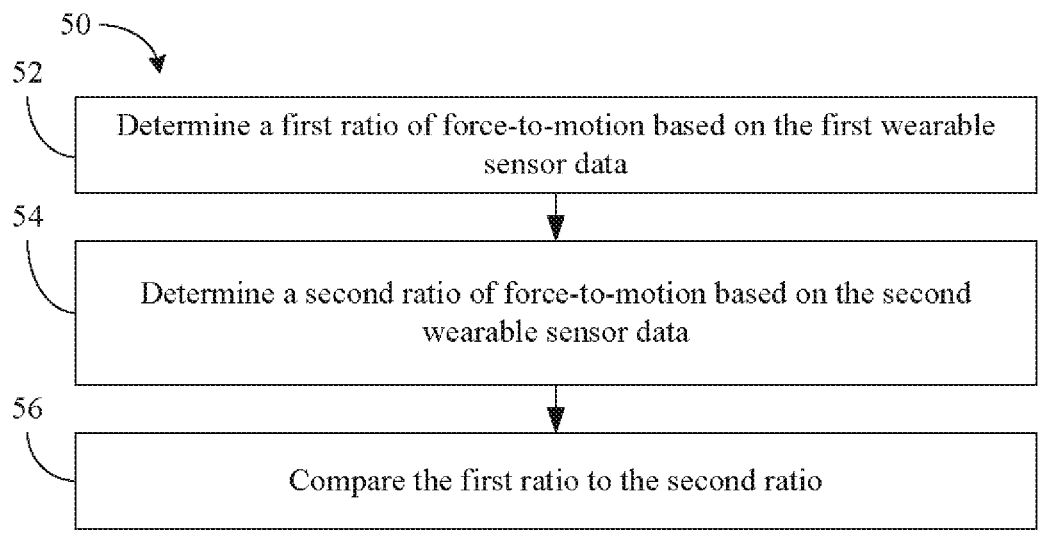
FIG. 4 is a block diagram of an example of a method of conducting effort normalizations according to an embodiment.

FIG. 4 shows a method 50 of conducting effort normalizations. The method 50, which may be readily incorporated into block 46 (FIG. 3), already discussed, may generally be implemented in, for example, the first wearable device 22 (FIGS. 2A and 2B), the fitness equipment 12, 14 (FIG. 1), and/or the fitness equipment 38 (FIG. 2C), already discussed. More particularly, the method 40 may be implemented in one or more modules as a set of logic instructions stored in a machine- or computer-readable storage medium such as RAM, ROM, PROM, firmware, flash memory, etc., in configurable logic such as, for example, PLAs, FPGAs, CPLDs, in fixed-functionality logic hardware using circuit technology such as, for example, ASIC, CMOS or TTL technology, or any combination thereof.

Illustrated processing block 52 provides for determining a first ratio of force-to-motion based on first wearable sensor data. For example, block 52 might determine that the user is generating 1000 N of foot pressure at a stride length of 2.5 ft. during a first fitness session on first fitness equipment. The first ratio may therefore be 400 N/ft. in such a scenario. Block 54 may determine a second ratio of force-to-motion based on second wearable sensor data. For example, block 54 might determine that the user (e.g., either the same user or a different user) is generating 900 N of foot pressure at a stride length of 3.0 ft. during a second fitness session on second fitness equipment. The second ratio may therefore be 300 N/ft. in such a scenario. Illustrated block 56 provides for comparing the first ratio to the second ratio, wherein the first ratio and the second ratio represent a unit of effort.

Thus, in the above example, block 56 might determine that the user is asserting less effort in the second fitness session. In such as case, the user may be prompted to assert more effort by, for example, increasing speed, incline and/or resistance. Other approaches may also be used to conduct the effort normalization. For example, the ratio may contain one of multiple factors including perspiration sensor data, temperature sensor data, heart rate sensor data, microphone data, camera feeds, blood flow data, environmental data (e.g., ambient temperature, air pressure/barometer, altitude), time data (e.g., early morning versus late evening), location data (e.g., usual location versus hotel while traveling), etc., that may also be indicative of the level of effort being asserted by the user. Moreover, different ratios/measures may be created for different groups based on, for example, data from a single user.

In some embodiments of the method 50, the motion in the force-to-motion ratio may be a virtual unit of motion. For example, exercise equipment is often calibrated to give the user a mileage estimate that corresponds to cycles at a given force. In the case of an exercise equipment that acts as a stationary bicycle, a revolution of the pedal at a given force level may count as a "distance" unit, even though the equipment is stationary. In some cases, a number of units of credit may be given, wherein the credit correlates with duration or required force. In this case, the motion in the force-to-motion ratio may be such a unit that is not correlated to an estimated distance.

Figure 5:
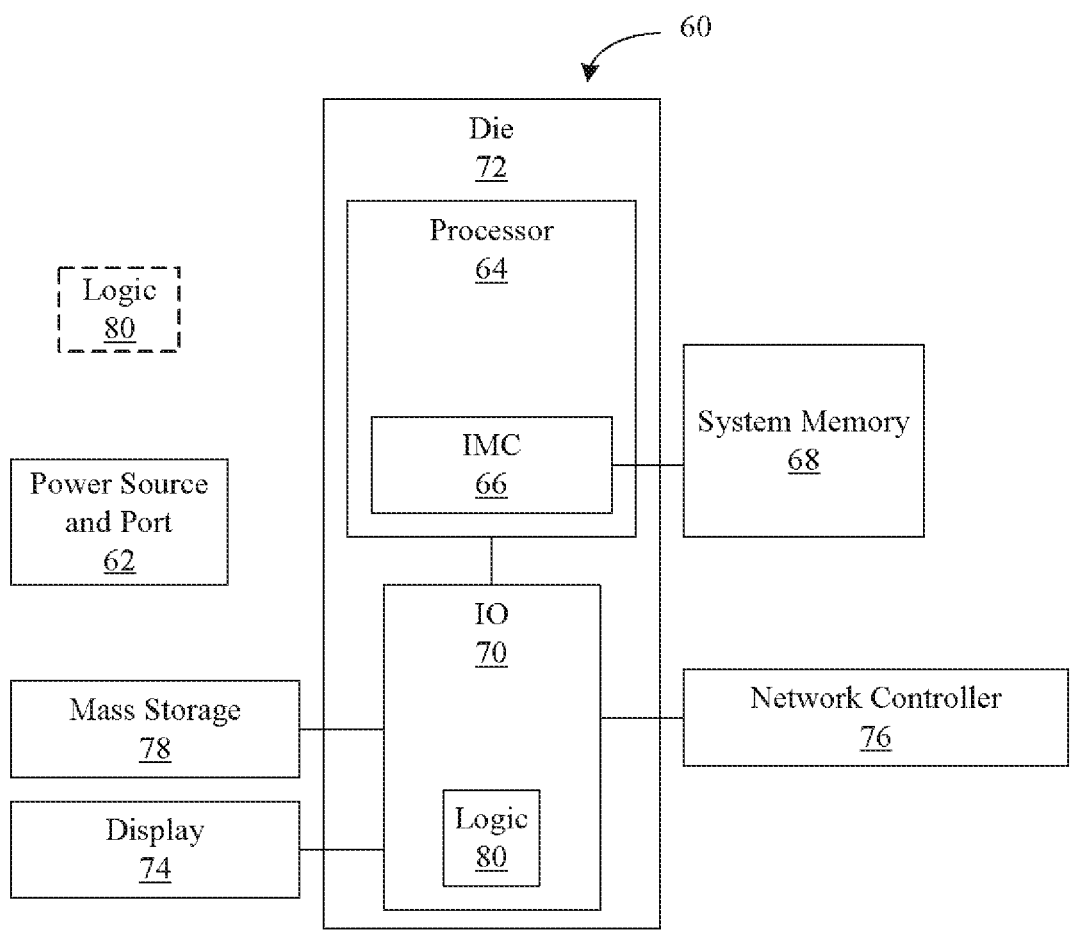
FIG. 5 is a block diagram of an example of a computing system according to an embodiment.

FIG. 5 shows a computing system 60. The computing system 60 may be part of an electronic device/platform having fitness functionality (e.g., treadmill, elliptical trainer, weight machine, weight set, stationary bike, step machine, bicycle, boat, or the like), computing functionality (e.g., personal digital assistant/PDA, notebook computer, tablet computer), communications functionality (e.g., smart phone), imaging functionality, media playing functionality (e.g., smart television/TV), wearable functionality (e.g., glove, watch, eyewear, headwear, footwear, jewelry), sensing functionality (e.g., Internet of Things/IoT device), etc., or any combination thereof. In the illustrated example, the system 60 includes a power source and port 62 to supply power to the system 60 and a processor 64 having an integrated memory controller (IMC) 66, which may communicate with system memory 68. The system memory 68 may include, for example, dynamic random access memory (DRAM) configured as one or more memory modules such as, for example, dual inline memory modules (DIMMs), small outline DIMMs (SODIMMs), etc.

The illustrated system 60 also includes an input output (10) module 70 implemented together with the processor 64 on a semiconductor die 72 as a system on chip (SoC), wherein the IO module 70 functions as a host device and may communicate with, for example, a display 74 (e.g., touch screen, liquid crystal display/LCD, light emitting diode/LED display), a network controller 76 (e.g., Bluetooth radio, Wi-Fi radio), and mass storage 78 (e.g., hard disk drive/HDD, optical disk, flash memory, etc.). The illustrated IO module 70 may include logic 80 to obtain first wearable sensor data associated with a first fitness session and first fitness equipment, obtain second wearable data associated with a second fitness session and second fitness equipment, and conduct an effort normalization between one or more settings of the second fitness equipment and one or more settings of the first fitness equipment based on the first wearable sensor data and the second wearable sensor data. Thus, the logic 80 may have functionality similar to that of the logic 22a (FIGS. 2A and 2B) and/or the logic 37 (FIG. 2C). Additionally, the logic 80 may implement one or more aspects of the method 40 (FIG. 3) and/or the method 50 (FIG. 4). The logic 80 may also be implemented elsewhere in the system 60. Accordingly, the semiconductor die 72 may function as a fitness session enhancement apparatus.

Techniques described herein may therefore address concerns over workout difficulty by gathering workout characteristics (e.g., using a low pass filter) of recorded sensor data to determine static inclination, speed and other configurable settings on the fitness equipment. Such an approach may ensure that the workout selection by a first user may be "replayed" for competitors. Although sensor data may only be shared within specified groups, the system may also use the data (e.g., as part of an opt-in agreement) to suggest other public groups/competitions in which the user may want to participate (e.g., to maintain or increase workout difficulty). The system may also take advantage of a single individual who uses multiple equipment instances. Such an approach may enable equipment comparisons to be calibrated from the same set of sensors and the same individual wearing those sensors. Measures from this individual might be weighted with other data gathered from individuals who do not use both sets of equipment (e.g., enabling that individual's data to improve the comparisons being made for other individuals).

Additionally, comparative "effort" may be determined on the basis of HR (heart rate), perspiration, weight, and environmental factors (e.g., humidity, temperature), and so forth. Simply put, techniques may provide for a "unit of effort" that explicitly measures comparative effort. Such an approach may be useful for individuals who maintain effort across a training regime—over time the individual becomes fitter and what was once an effortful workout may become easier. The unit of effort may therefore enable the user to maintain effort across changing levels of fitness.

Physical Resistance Measurement and Automatic Adjustment

In particular example embodiments, air/wind resistance can be measured and automatically adjusted for athletic activities, such as riding a bicycle, and for related fitness equipment, such as a bicycle. Tire pressure and other sources of friction can also be measured and automatically adjusted in such athletic activities. Additionally, water resistance can be measured and automatically adjusted for athletic activities, such as rowing or kayaking, and for related fitness equipment, such as a kayak, shell, or boat. Various examples of these measurement and automatic adjustment features in the example embodiments are provided below.

Air/Wind Resistance Measurement

Figure 6:
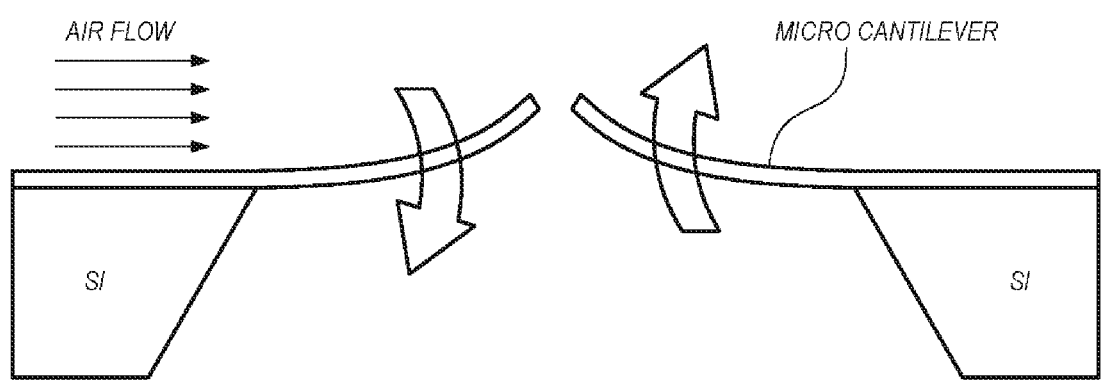
FIG. 6 illustrates an example of a conventional microelectromechanical systems (MEMS)-based air flow velocity sensor.

Many conventional low power microelectromechanical systems (MEMS) sensor implementations have been proposed for measuring wind resistance. For example, a conventional MEMs-based air flow velocity sensor is illustrated in FIG. 6 (See "A Microcantilever-Based Gas Flow Sensor for Flow Rate and Direction Detection", Yu-Hsiang Wang, Tzu-Han Hsueh, DYU, Taiwan; Rong-Hua Ma, CMA, Taiwan; Chia-Yen Lee, D W, Taiwan; Lung-Ming Fu, NPUST, Taiwan; Po-Cheng Chou, STU, Taiwan; and Chien-Hsiung Tsai, NPUST, Taiwan; *Collection of Papers Presented at the Symposium on Design, Test, Integration and Packaging of MEMS/MOEMS,* 2008, 9-11 April, 2008, pg. 142; herein Wang et al.). As shown in FIG. 6, the Wang et al. air flow velocity sensor detects air flow velocity by measuring the change in resistance of the piezoelectric resistors deposited on the cantilever beams as the beam deforms under the effect of the passing airflow. The airflow direction can be obtained by comparing the resistance variation difference between the upstream and downstream cantilever beams to evaluate the airflow angle. The Wang et al. air flow sensor can be sized at about two square centimeters and can measure both air flow velocity and direction. Given the relatively small size of the air flow sensor, the device can be conveniently integrated into a wearable device or a garment that can be worn by a user and participant in an athletic activity. For example, such sensors can be worn as a broach-like wearable, a medallion, a pin, or a patch. The sensor can also be sewn into a garment, attached to a garment using a hook and loop mechanism, adhesive, or other attachment mechanism. As a result, the air flow experienced by a user (e.g., a bicycle rider) can be readily and continuously monitored during an athletic activity. The air flow data captured by the air flow sensor can be transferred to a controller on the bicycle, or other fitness equipment, using a conventional wireless data connection and protocol. For example, the air flow sensor and the controller can be implemented with or within the system 60 described above. It will be apparent to those of ordinary skill in the art in view of the disclosure herein that other types of air flow sensors can similarly be used.

An Example Embodiment for Use with Bicycles

In a particular example embodiment, air/wind resistance and tire pressure, among other types of physical resistance, can be measured and automatically adjusted for athletic activities, such as riding a bicycle equipped with a hybrid drive mechanism. For example, a conventional implementation of a hybrid drive mechanism for a bicycle is known as the, "Copenhagen Wheel," which provides hybrid, controller-assisted power or resistance drive for bicycles. (See, e.g., Germano, Beth, "Cambridge Company Creates Wheel That Turns Any Bicycle into a Hybrid Electric," CBS Boston, http://boston.cbslocal.com/2013/12/06, (Dec. 6, 2013). The Copenhagen Wheel is a bicycle wheel and drive mechanism, attachable to a bicycle, that stores and delivers electric energy to power the bicycle. Energy comes from an external battery charger, and from regenerative braking when the rider back-pedals as in a coaster brake. The resulting hybrid-driven bicycle is a pedelec, wherein the rider's pedaling is assisted by a small, built-in electric motor and a lithium ion battery. The conventional Copenhagen Wheel can be controlled by a smartphone application (app), a wireless computing platform, or a controller such as the system 60 described above. As described in more detail below, the controller can measure the physical resistance being experienced by the rider and analyze the effort being expended by the rider, the course topography, and the pedaling activity to determine whether to deliver power (e.g., a thrust force) or a resistance force to the bicycle via the Copenhagen Wheel subsystem.

Figure 7:
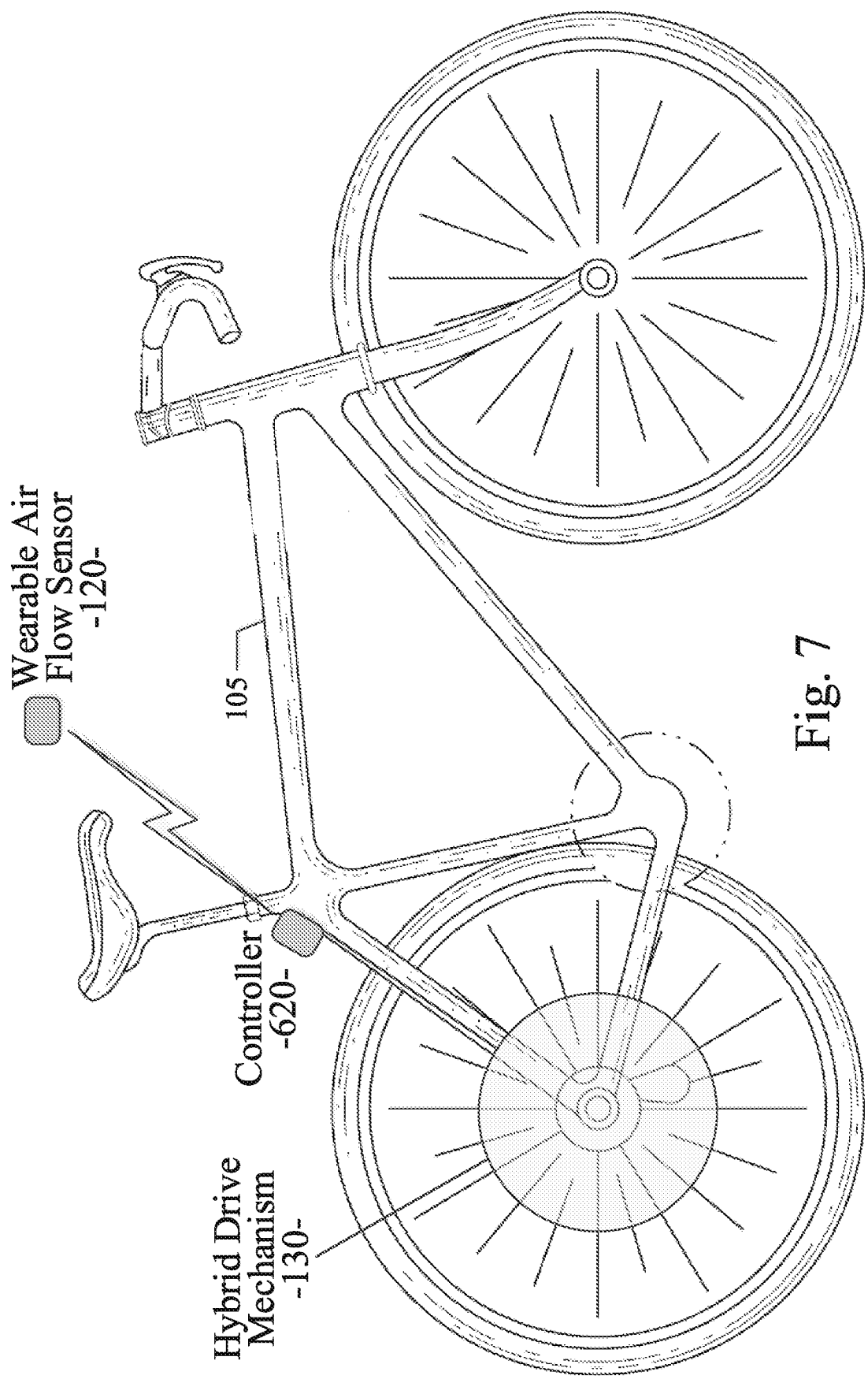
FIG. 7 illustrates an example embodiment including a bicycle equipped with a hybrid drive mechanism.

Referring now to FIG. 7, a bicycle 105 equipped with a hybrid drive mechanism 130 is shown. As described above, the hybrid drive mechanism 130 can include the components of the conventional Copenhagen Wheel, such as an electric motor, battery, drive mechanism, subsystem control module, and smartphone app interface. In an example embodiment disclosed herein, the Copenhagen Wheel can further include an interface to the controller described in more detail below. It will be apparent to those of ordinary skill in the art in view of the disclosure herein that other types of hybrid drive mechanisms for a bicycle can similarly be used.

The example embodiment shown in FIG. 7 includes a controller 620 and a user-wearable air flow sensor 120. The wearable air flow sensor 120 can be implemented as the MEMs-based air flow sensor as described above. The air flow sensor 120 can be worn by a rider of bicycle 105. In an alternative embodiment, the air flow sensor 120 can be attached directly to the bicycle 105. As described above, the air flow sensor 120 can detect the air flow velocity and direction being experienced by the rider in real time. Sensor data indicative of the air flow velocity and direction can be periodically transferred to controller 620 via a wired or wireless data connection.

Controller 620 can be configured in an example embodiment to be a microcontroller (e.g., an MSP430, or other type of data processor, controller, microcontroller, or the like). It will be apparent to those of ordinary skill in the art in view of the disclosure herein that any of a variety of standard data processors, controllers, microcontrollers, application specific integrated circuits (ASICs), field programmable gate arrays (FPGAs), discrete logic circuits, or other circuitry or logic can be similarly used as the controller 620 of the example embodiments. In an alternative embodiment, the controller 620 can be integrated into the hybrid drive mechanism 130 or integrated into the subsystem control module of the hybrid drive mechanism 130. In any case, the controller 620 can receive the sensor data produced by the air flow sensor 120. In a particular embodiment, controller 620 can include a global positioning system (GPS) receiver and GPS logic for determining a geographical location, speed, and direction of travel of the bicycle at any point in time. The controller 620 can use the air flow sensor data and the GPS data to determine the geographical location, speed, and direction of travel of the bicycle relative to the current wind being experienced by the bicycle and rider. This data can be transferred to the smartphone app or other external computing platform for further processing to determine if an adjustment is needed to the physical resistance of the bicycle 105 to achieve a desired level of performance relative to other bicycle riders or relative to a rider's own previous performance history. In an alternative embodiment, the sensor data and the GPS data can be processed directly by the controller 620 if a smartphone app or other external computing platform is not available or not desired. As a result, the controller 620 can use one or more sensors to measure the physical resistance being experienced by the rider. The controller 620 can also use sensor data to determine a level of effort being expended by the rider.

Physical Resistance Adjustment

The Copenhagen Wheel described above, and as modified by the example embodiments described herein, provides a way to automatically adjust physical resistance on bicycle wheels. For example, the Copenhagen Wheel uses a friction charging system similar to a hybrid car in that resistance while braking charges the battery. Copenhagen Wheels reuse rotational force to create resistance. The charging mechanism in the recharge subsystem creates smooth drag on the wheel rotation. Such a mechanism can be used to increase friction for one rider (e.g., automatically increase wheel drag) and speed up another rider (e.g., automatically increase wheel thrust). As a result, an example embodiment can automatically apply an increased physical resistance for a rider of greater ability or add power (e.g., automatically increase wheel thrust) for a rider of lesser ability. This enables the example embodiment to dynamically adjust physical resistance and thereby match the performance levels of riders with varying athletic abilities during an athletic activity. In a similar manner, the resistance applied to the wheel of a stationary bike can be automatically adjusted to match the performance levels of a plurality of stationary bike riders. In another example embodiment, the controller 620 can be configured to interface with a tire pressure adjustment mechanism. The tire pressure adjustment mechanism can be controlled to automatically measure tire pressure and to release tire pressure to increase tire friction and thereby increase physical resistance for a rider of greater ability. This embodiment can automatically increase physical resistance for a particular rider through tire pressure adjustment. The example embodiments described above relate to bicycles and bicycle riders; but, alternative embodiments can apply the same or similar systems and processes to any object moved by the user that has the potential for fitness training or athletic competition.

In a machine weights example, dynamic physical resistance can be created by the machine. Such systems already exist for manual adjustment of machine weights (e.g., mechanical or magnetic resistance). The embodiments described herein can be applied to the automatic adjustment of machine weights based on a particular participant's performance relative to other participants or to the particular participant's performance in previous fitness workout sessions. An example embodiment can be used to apply dynamic weight adjustments for a user based on a measure of the current performance level of the user. For example, a measure of the current performance level of the user can be based on a velocity, number of repetitions, or extent of movement of the current weight and the performance of the user in previous workouts. A decrease in the user's performance level may be indicative of an increase in the user's level of fatigue at the current weight. In response, the example embodiment can automatically cause the weight machine to decrease the weight and thereby equalize the user's performance level.

In the various embodiments described above, the user's performance level is used as a basis for automatically determining if physical resistance in an athletic activity should be increased or decreased by the disclosed systems and methods. The user's performance level can be compared with the performance levels of other participants in a particular athletic activity or set of activities. Additionally, the user's performance level can be compared with the performance levels of the same user at previous points in time or in previous athletic activities. In either case, an example embodiment keeps a record of the performance levels for each user for each athletic activity. This user performance data is maintained in user profiles as described below.

Profiles and Monitoring

Figure 8:
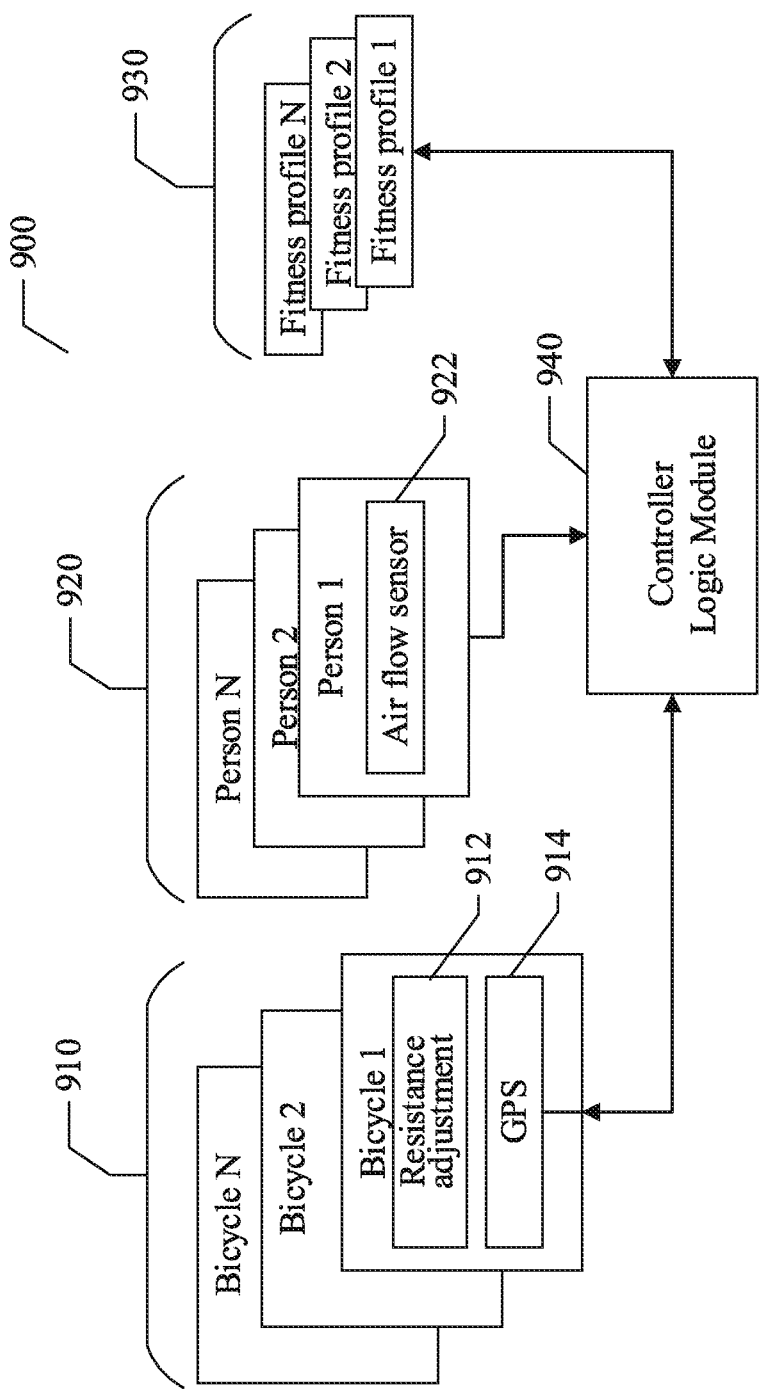
FIG. 8 illustrates an example embodiment of user profiles and position monitoring to enable a process of matching or conforming the athletic performance levels across two or more users.

Referring now to FIG. 8 in an example embodiment, the use of user profiles and position monitoring enables a process of matching or conforming the athletic performance levels across two or more users. User times, distances, speeds, heights, weights, calories burned, or other performance metrics in comparable athletic activities can allow the system to rate and rank performance levels of each participant. The system can then assign resistance levels to the better performing participants in an athletic activity to handicap their performance relative to the other participants in the activity who may not be performing as well. Using any of the techniques described above, the system can then adjust the physical resistance levels for one or more of the participants in the activity to match the performance of each of the participants. As a result, each of the participants can perform the athletic activity with a substantially equivalent performance level relative to the other participants, which makes the activity more enjoyable for all of the participants. The system of an example embodiment can both learn and make adjustments on the fly by monitoring the relative performance level of the participants. For example, the system can monitor the position of bicycle riders in a biking activity or the position of rowers in a boating activity. The system can also learn how various adjustments to resistance correspond to performance changes by monitoring the relative positions of riders under various circumstances and then monitoring the position changes that occur when adjustments to resistance are effected. The system can also learn across users through anonymous data sharing.

FIG. 8 illustrates the fitness profiles 930 that can be associated and retained for a given person involved in one or more athletic activities. In an example embodiment, the fitness profile 930 for each person can contain one or more of the following information elements, depending on a given athletic activity application:

1. Times needed to complete particular fitness courses or athletic activities;
2. Number of reps per minute at a given weight;
3. Trends in any of the above, such as an average percent improvement per session;
4. Length of time since the last workout;
5. User response to a force adjustment (e.g., with a 5% increase in wheel resistance, how that user performed on the same course under the same conditions);
6. Record of how previous force adjustments correlated that user's performance to the athletic performance of workout friends (e.g., people who compete or just go together on the same course);
7. User performance variance under various weather conditions including temperature, humidity, and wind resistance.

It will be apparent to those of ordinary skill in the art in view of the disclosure herein that other data can be similarly stored and associated with a particular participant's profile. Datasets 910 and 920 can be maintained to save information related to any of a plurality of fitness equipment (e.g., bicycle data 910) or a plurality of users/participants in one or more athletic activities (e.g., person data 920). The data maintained in these datasets can be used to uniquely identify a particular fitness device or person along with the characteristics, performance, and/or status of each fitness device or person. Dataset 910 can include, for example, information associated with a GPS device 914 and/or a physical resistance adjustment 912 applied to or associated with a particular fitness device. Similarly, dataset 920 can include, for example, information associated with a sensor 922 being worn by a particular user. The sensor information 922 can be used to identify the presence and characteristics of the sensor being worn or used by the particular user. A fitness profile for each user can be stored in fitness profile dataset 930. As described above, the fitness profile for each person can contain a variety of information elements that record a variety of parameters associated with the athletic performance of a particular person in current and prior athletic activities, the performance trends for the person, the preferences, strengths, weaknesses, responses to physical resistance adjustments, and the like. In an embodiment, the system of an example embodiment can store a particular participant's performance data and related physical resistance adjustments, generated in the manner described above, into a corresponding fitness profile 930.

Given the datasets 910, 920, and 930 as described above, the system of an example embodiment can compare the performance levels of a plurality of participants in an athletic activity. In view of this performance comparison, the system can automatically increase resistance in the bicycle wheel of bicycle 1 and bicycler/rider 1, for example, to make the predicted time to ride a given course equal to the time required by bicycler/rider 2. In this case, bicycler/rider 2 may have no applied physical resistance; because, the fitness profile 930 for bicycler/rider 2 indicates that he or she requires more time to complete the course than bicycler/rider 1 under a condition of no resistance for bicycler/rider 2.

As shown in FIG. 8, the datasets 910, 920, and 930 are each accessible to controller logic module 940. The controller logic module 940 is a logic module that coordinates how a given person's applied physical resistance should be adjusted to achieve a desired level of performance (e.g., the estimated time to complete an athletic activity that is equivalent to a rider of differing ability). The controller logic module 940 can represent software, firmware, or electronic logic that can be executed or controlled by controller 620. Because the controller logic module 940 has access to the datasets for each of the fitness devices (e.g., dataset 910), persons (e.g., dataset 920), and fitness profiles (e.g., dataset 930), the controller logic module 940 can perform the comparisons described above across a plurality of devices and people. Additionally, the controller logic module 940 may perform "tests" of a given user, for example, by implementing a physical resistance level for that user to see how the user's athletic performance is impacted. This data can be stored in the person's fitness profile 930.

In a particular application of the described embodiments for use with bicycles, the factor of wind resistance can be an important consideration related to bicycle riding conditions. The disclosure provided above describes how wind resistance can be measured. For example, FIG. 6, as described above, illustrates an example of existing sensor devices that measure air flow. As also described above, such air flow sensors can be implemented as a user-wearable device. In the case of tracking a user's performance, wind resistance effect data can be included in a user's fitness profile 930. In some cases, the "competing user", or the particular user with whom another user is being compared from an athletic performance perspective, may actually be the same user's predicted performance given current conditions. This can apply to usage models that do not include separate exercise equipment. If the user expends more effort to overcome a strong headwind, for example, the user can be given credit for a more successful performance.

An Example Embodiment for Use with Boats

Figure 9:
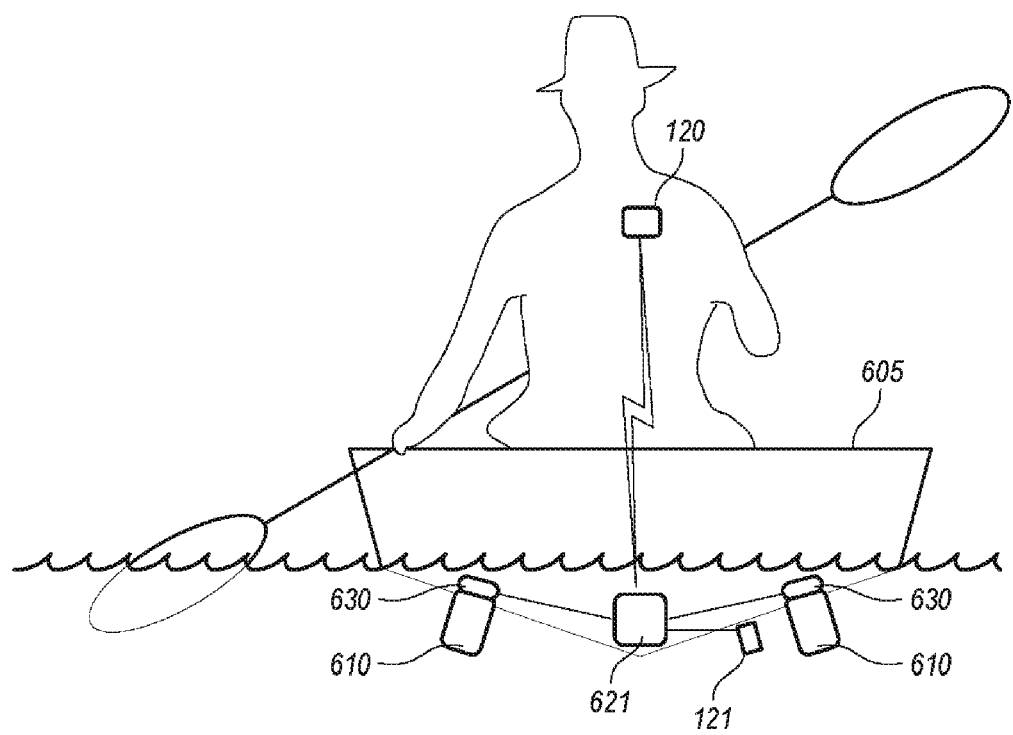
FIGS. 9 and 10 illustrate an example embodiment including a boat equipped with automatically adjustable resistance rudders.
Figure 10:
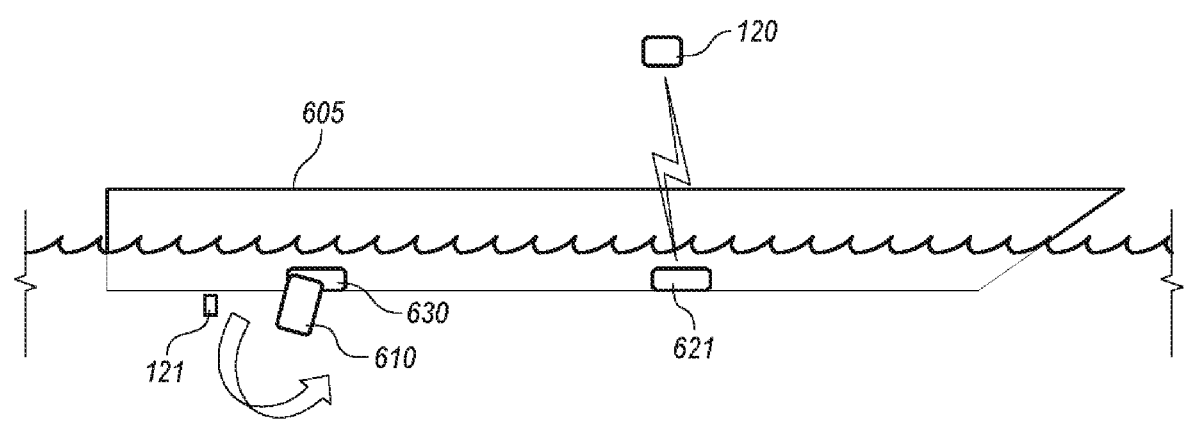

A boating example for measuring water resistance and for adjusting physical resistance as a boat moves through water is described with reference to FIGS. 9 and 10. In particular, FIGS. 9 and 10 illustrate an example embodiment including a boat 605 equipped with automatically adjustable resistance rudders 610. In a boating example, automatically adjustable resistance rudders 610 can create additional (or less) water resistance to cause the performance of a particular paddler to conform to the performance of other paddlers in a particular boating activity. If two people of varying ability are paddling together, the system of an example embodiment can match the performance levels of each of the paddlers by increasing the water resistance on one paddler's boat, or making an equivalent athletic activity under different conditions, such as going with or without the current. The resistance rudders 610 of each of the boats in a boating activity can be automatically adjusted as the system detects variations between the performance levels of a plurality of participants in a boating activity (e.g., similar to the biking example described above). As shown in, FIGS. 9 and 10, the boat 605 can be equipped with automatically adjustable resistance rudders 610 and rudder actuators 630 to control the degree of deflection of the resistance rudders 610 under control of the controller 621. The controller 621 can also be in data communication with an air flow sensor 120 as described above and a water flow sensor 121. Water flow sensor 121 can use conventional technology to measure the speed of the boat 605 through the water. Alternatively, a GPS receiver can be used to obtain position and speed information. The controller 621 can use the sensor data received from the air flow sensor 120 and the water flow sensor/GPS 121 to determine a performance level for the particular boat 605. As described above, this performance level can be compared with the performance levels of other boats in an athletic activity. As a result of this comparison, the controller 621 can determine if an adjustment is needed to the resistance rudders 610 to conform the performance of boat 605 to a desired performance level.

Referring now to FIG. 11, a processing flow diagram illustrates an example embodiment of a method 1100 as described herein. The method 1100 of an example embodiment includes: measuring a level of physical resistance in an athletic activity (processing block 1110); generating sensor data indicative of the measured level of physical resistance (processing block 1120); using the sensor data to determine if the measured level of physical resistance will achieve a desired performance level in the athletic activity (processing block 1130); and automatically generating control signals to adjust the level of physical resistance if the measured level of physical resistance is unlikely to achieve the desired performance level in the athletic activity (processing block 1140).

Embodiments described herein are applicable for use with all types of semiconductor integrated circuit ("IC") chips. Examples of these IC chips include but are not limited to processors, controllers, chipset components, programmable logic arrays (PLAs), memory chips, network chips, systems on chip (SoCs), SSD/NAND controller ASICs, and the like. In addition, in some of the drawings, signal conductor lines are represented with lines. Any represented signal lines, whether or not having additional information, may actually comprise one or more signals that may travel in multiple directions and may be implemented with any suitable type of signal scheme, e.g., digital or analog lines implemented with differential pairs, optical fiber lines, and/or single-ended lines.

Example sizes/models/values/ranges may have been given, although embodiments are not limited to the same. As manufacturing techniques (e.g., photolithography) mature over time, it is expected that devices of smaller size can be manufactured. In addition, well-known power/ground connections to integrated circuit (IC) chips and other components may or may not be shown within the figures, for simplicity of illustration and discussion, and so as not to obscure certain aspects of the embodiments. Further, arrangements may be shown in block diagram form in order to avoid obscuring embodiments, and also in view of the fact that specifics with respect to implementation of such block diagram arrangements are highly dependent upon the platform within which the embodiment is to be implemented, i.e., such specifics should be well within purview of one of ordinary skill in the art. Where specific details (e.g., circuits) are set forth in order to describe example embodiments, it should be apparent to one of ordinary skill in the art that embodiments can be practiced without, or with variation of, these specific details. The description is thus to be regarded as illustrative instead of limiting.

The term "coupled" may be used herein to refer to any type of relationship, direct or indirect, between the components in question, and may apply to electrical, mechanical, fluid, optical, electromagnetic, electromechanical or other connections. In addition, the terms "first", "second", etc. may be used herein only to facilitate discussion, and carry no particular temporal or chronological significance unless otherwise indicated.

Controllers 620 and 621 and sensor 120 may include one or more wireless transceivers, in some embodiments. Each of the wireless transceivers may be implemented as physical wireless adapters or virtual wireless adapters, sometimes referred to as "hardware radios" and "software radios," respectively. A single physical wireless adapter may be virtualized (e.g., using software) into multiple virtual wireless adapters. A physical wireless adapter typically connects to a hardware-based wireless access point. A virtual wireless adapter typically connects to a software-based wireless access point, sometimes referred to as a "SoftAP." For instance, a virtual wireless adapter may allow ad hoc communications between peer devices, such as a smartphone and a desktop computer or notebook computer. Various embodiments may use a single physical wireless adapter implemented as multiple virtual wireless adapters, multiple physical wireless adapters, multiple physical wireless adapters each implemented as multiple virtual wireless adapters, or some combination thereof. The example embodiments described herein are not limited in this respect.

The wireless transceivers may include or implement various communication techniques to allow the controllers 620 and 621 and sensor 120 to communicate with other electronic devices. For instance, the wireless transceivers may implement various types of standard communication elements designed to be interoperable with a network, such as one or more communications interfaces, network interfaces, network interface cards (NIC), radios, wireless transmitters/receivers (transceivers), wired and/or wireless communication media, physical connectors, and so forth.

By way of example, and not limitation, communication media includes wired communications media and wireless communications media. Examples of wired communications media may include a wire, cable, metal leads, printed circuit boards (PCB), backplanes, switch fabrics, semiconductor material, twisted-pair wire, co-axial cable, fiber optics, a propagated signal, and so forth. Examples of wireless communications media may include acoustic, radio-frequency (RF) spectrum, infrared and other parts of the spectrum, and other wireless media.

In various embodiments, the controllers 620 and 621 and sensor 120 may implement different types of wireless transceivers. Each of the wireless transceivers may implement or utilize a same or different set of communication parameters to communicate information between various electronic devices. In one embodiment, for example, each of the wireless transceivers may implement or utilize a different set of communication parameters to communicate information between controllers 620 and 621 and sensor 120 and any number of other devices. Some examples of communication parameters may include without limitation a communication protocol, a communication standard, a radio-frequency (RF) band, a radio, a transmitter/receiver (transceiver), a radio processor, a baseband processor, a network scanning threshold parameter, a radio-frequency channel parameter, an access point parameter, a rate selection parameter, a frame size parameter, an aggregation size parameter, a packet retry limit parameter, a protocol parameter, a radio parameter, modulation and coding scheme (MCS), acknowledgement parameter, media access control (MAC) layer parameter, physical (PHY) layer parameter, and any other communication parameters affecting operations for the wireless transceivers. The example embodiments described herein are not limited in this respect.

In various embodiments, the wireless transceivers may implement different communication parameters offering varying bandwidths, communications speeds, or transmission ranges. For instance, a first wireless transceiver may include a short-range interface implementing suitable communication parameters for shorter range communication of information, while a second wireless transceiver may include a long-range interface implementing suitable communication parameters for longer range communication of information.

In various embodiments, the terms "short-range" and "long-range" may be relative terms referring to associated communications ranges (or distances) for associated wireless transceivers as compared to each other rather than an objective standard. In one embodiment, for example, the term "short-range" may refer to a communications range or distance for the first wireless transceiver that is shorter than a communications range or distance for another wireless transceiver implemented for controllers 620 and 621 and sensor 120, such as a second wireless transceiver. Similarly, the term "long-range" may refer to a communications range or distance for the second wireless transceiver that is longer than a communications range or distance for another wireless transceiver implemented for the controllers 620 and 621 and sensor 120, such as the first wireless transceiver. The example embodiments described herein are not limited in this respect.

In one embodiment, for example, the wireless transceiver may include a radio designed to communicate information over a wireless personal area network (WPAN) or a wireless local area network (WLAN). The wireless transceiver may be arranged to provide data communications functionality in accordance with different types of lower range wireless network systems or protocols. Examples of suitable WPAN systems offering lower range data communication services may include a Bluetooth™ system as defined by the Bluetooth Special Interest Group, an infra-red (IR) system, an Institute of Electrical and Electronics Engineers (IEEE™) 802.15 system, a DASH7 system, wireless universal serial bus (USB), wireless high-definition (HD), an ultra-side band (UWB) system, and similar systems. Examples of suitable WLAN systems offering lower range data communications services may include the IEEE 802.xx series of protocols, such as the IEEE 802.11a/b/g/n series of standard protocols and variants (also referred to as "WiFi"). It may be appreciated that other wireless techniques may be implemented. The example embodiments described herein are not limited in this respect.

In one embodiment, for example, the wireless transceiver may include a radio designed to communicate information over a wireless metropolitan area network (WMAN), a wireless wide area network (WWAN), or a cellular radio-telephone system. Another wireless transceiver may be arranged to provide data communications functionality in accordance with different types of longer range wireless network systems or protocols. Examples of suitable wireless network systems offering longer range data communication services may include the IEEE 802.xx series of protocols, such as the IEEE 802.11a/b/g/n series of standard protocols and variants, the IEEE 802.16 series of standard protocols and variants, the IEEE 802.20 series of standard protocols and variants (also referred to as "Mobile Broadband Wireless Access"), and so forth. Alternatively, the wireless transceiver may include a radio designed to communicate information across data networking links provided by one or more cellular radiotelephone systems. Examples of cellular radiotelephone systems offering data communications services may include GSM with General Packet Radio Service (GPRS) systems (GSM/GPRS), CDMA/1xRTT systems, Enhanced Data Rates for Global Evolution (EDGE) systems, Evolution Data Only or Evolution Data Optimized (EV-DO) systems, Evolution For Data and Voice (EV-DV) systems, High Speed Downlink Packet Access (HSDPA) systems, High Speed Uplink Packet Access (HSUPA), and similar systems. It may be appreciated that other wireless techniques may be implemented. The example embodiments described herein are not limited in this respect.

Although not shown, controllers 620 and 621 and sensor 120 may further include one or more device resources commonly implemented for electronic devices, such as various computing and communications platform hardware and software components typically implemented by a personal electronic device. Some examples of device resources may include without limitation a co-processor, a graphics processing unit (GPU), a chipset/platform control logic, an input/output (I/O) device, computer-readable media, network interfaces, portable power supplies (e.g., a battery), application programs, system programs, and so forth. The example embodiments described herein are not limited in this respect.

Included herein is a set of logic flows representative of example methodologies for performing novel aspects of the disclosed architecture. While, for purposes of simplicity of explanation, the one or more methodologies shown herein are shown and described as a series of acts, those of ordinary skill in the art will understand and appreciate that the methodologies are not limited by the order of acts. Some acts may, in accordance therewith, occur in a different order and/or concurrently with other acts from those shown and described herein. For example, those of ordinary skill in the art will understand and appreciate that a methodology can alternatively be represented as a series of interrelated states or events, such as in a state diagram. Moreover, not all acts illustrated in a methodology may be required for a novel implementation. A logic flow may be implemented in software, firmware, and/or hardware. In software and firmware embodiments, a logic flow may be implemented by computer executable instructions stored on at least one non-transitory computer readable medium or machine readable medium, such as an optical, magnetic or semiconductor storage. The example embodiments disclosed herein are not limited in this respect.

The various elements of the example embodiments as previously described with reference to the figures may include various hardware elements, software elements, or a combination of both. Examples of hardware elements may include devices, logic devices, components, processors, microprocessors, circuits, processors, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), memory units, logic gates, registers, semiconductor device, chips, microchips, chip sets, and so forth. Examples of software elements may include software components, programs, applications, computer programs, application programs, system programs, software development programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. However, determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints, as desired for a given implementation.

The example embodiments described herein provide a technical solution to a technical problem. The various embodiments improve the functioning of the electronic device by providing systems and methods for measuring and adjusting physical resistance for athletic activities and fitness equipment. The various embodiments also serve to transform the state of various system components based on a dynamically determined system context. Additionally, the various embodiments effect an improvement in a variety of technical fields including the fields of dynamic data processing, fitness equipment operational management regulation, mobile computing, information sharing, and mobile communications.

Figure 12:
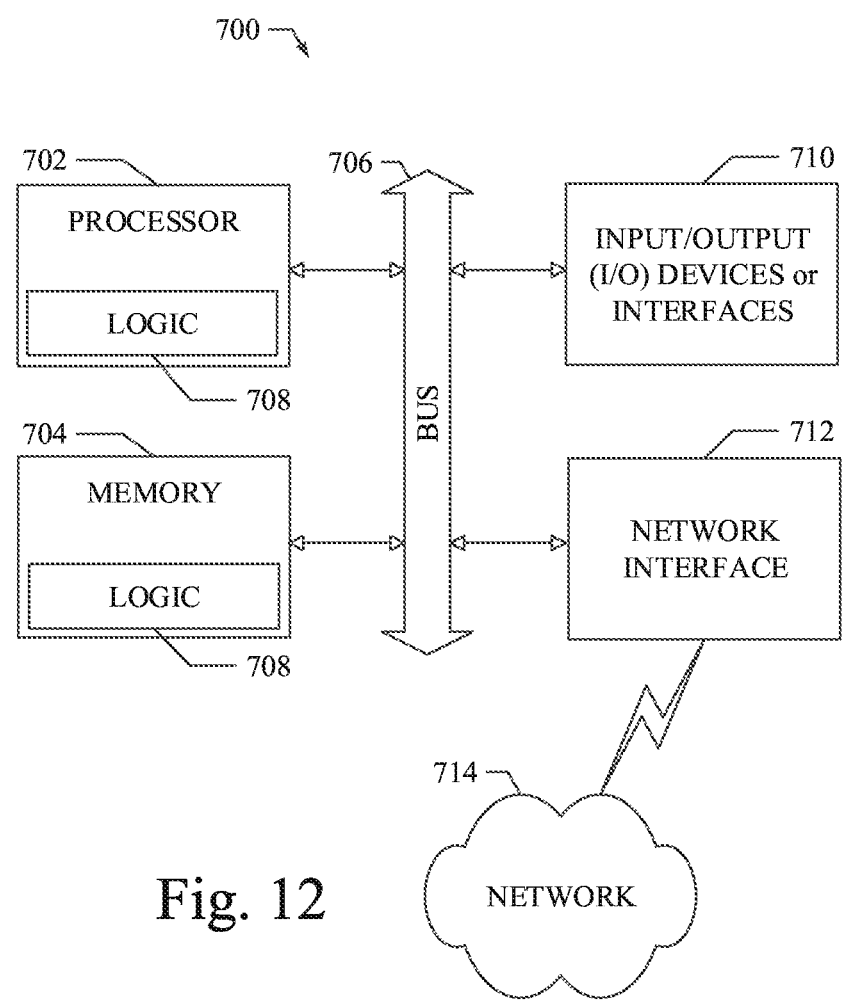
FIG. 12 shows a diagrammatic representation of a machine in the example form of a mobile computing and/or communication system within which a set of instructions when executed and/or processing logic when activated may cause the machine to perform any one or more of the methodologies described and/or claimed herein.

FIG. 12 shows a diagrammatic representation of a machine in the example form of an electronic device, such as a mobile computing and/or communication system 700 within which a set of instructions when executed and/or processing logic when activated may cause the machine to perform any one or more of the methodologies described and/or claimed herein. In alternative embodiments, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a personal computer (PC), a laptop computer, a tablet computing system, a Personal Digital Assistant (PDA), a cellular telephone, a smartphone, a web appliance, a set-top box (STB), a network router, switch or bridge, or any machine capable of executing a set of instructions (sequential or otherwise) or activating processing logic that specify actions to be taken by that machine. Further, while only a single machine is illustrated, the term "machine" can also be taken to include any collection of machines that individually or jointly execute a set (or multiple sets) of instructions or processing logic to perform any one or more of the methodologies described and/or claimed herein.

The example mobile computing and/or communication system 700 includes a data processor 702 (e.g., a System-on-a-Chip [SoC], general processing core, graphics core, and optionally other processing logic) and a memory 704, which can communicate with each other via a bus or other data transfer system 706. The mobile computing and/or communication system 700 may further include various input/output (I/O) devices and/or interfaces 710, such as a touchscreen display and optionally a network interface 712. In an example embodiment, the network interface 712 can include one or more radio transceivers configured for compatibility with any one or more standard wireless and/or cellular protocols or access technologies (e.g., 2nd (2G), 2.5, 3rd (3G), 4th (4G) generation, and future generation radio access for cellular systems, Global System for Mobile communication (GSM), General Packet Radio Services (GPRS), Enhanced Data GSM Environment (EDGE), Wideband Code Division Multiple Access (WCDMA), LTE, CDMA2000, WLAN, Wireless Router (WR) mesh, and the like). Network interface 712 may also be configured for use with various other wired and/or wireless communication protocols, including TCP/IP, UDP, SIP, SMS, RTP, WAP, CDMA, TDMA, UMTS, UWB, WiFi, WiMax, Bluetooth™, IEEE 802.11x, and the like. In essence, network interface 712 may include or support virtually any wired and/or wireless communication mechanisms by which information may travel between the mobile computing and/or communication system 700 and another computing or communication system via network 714.

The memory 704 can represent a machine-readable medium on which is stored one or more sets of instructions, software, firmware, or other processing logic (e.g., logic 708) embodying any one or more of the methodologies or functions described and/or claimed herein. The logic 708, or a portion thereof, may also reside, completely or at least partially within the processor 702 during execution thereof by the mobile computing and/or communication system 700. As such, the memory 704 and the processor 702 may also constitute machine-readable media. The logic 708, or a portion thereof, may also be configured as processing logic or logic, at least a portion of which is partially implemented in hardware. The logic 708, or a portion thereof, may further be transmitted or received over a network 714 via the network interface 712. While the machine-readable medium of an example embodiment can be a single medium, the term "machine-readable medium" should be taken to include a single non-transitory medium or multiple non-transitory media (e.g., a centralized or distributed database, and/or associated caches and computing systems) that store the one or more sets of instructions. The term "machine-readable medium" can also be taken to include any non-transitory medium that is capable of storing, encoding or carrying a set of instructions for execution by the machine and that cause the machine to perform any one or more of the methodologies of the various embodiments, or that is capable of storing, encoding or carrying data structures utilized by or associated with such a set of instructions. The term "machine-readable medium" can accordingly be taken to include, but not be limited to, solid-state memories, optical media, and magnetic media.

With general reference to notations and nomenclature used herein, the description presented herein may be disclosed in terms of program procedures executed on a computer or a network of computers. These procedural descriptions and representations may be used by those of ordinary skill in the art to convey their work to others of ordinary skill in the art.

A procedure is generally conceived to be a self-consistent sequence of operations performed on electrical, magnetic, or optical signals capable of being stored, transferred, combined, compared, and otherwise manipulated. These signals may be referred to as bits, values, elements, symbols, characters, terms, numbers, or the like. It should be noted, however, that all of these and similar terms are to be associated with the appropriate physical quantities and are merely convenient labels applied to those quantities. Further, the manipulations performed are often referred to in terms such as adding or comparing, which operations may be executed by one or more machines. Useful machines for performing operations of various embodiments may include general-purpose digital computers or similar devices. Various embodiments also relate to apparatus or systems for performing these operations. This apparatus may be specially constructed for a purpose, or it may include a general-purpose computer as selectively activated or reconfigured by a computer program stored in the computer. The procedures presented herein are not inherently related to a particular computer or other apparatus. Various general-purpose machines may be used with programs written in accordance with teachings herein, or it may prove convenient to construct more specialized apparatus to perform methods described herein.

In various embodiments as described herein, example embodiments include at least the following examples.

An apparatus comprising: a sensor to measure a level of physical resistance in an athletic activity and to generate sensor data indicative of the measured level of physical resistance; and a controller to receive the sensor data, to determine if the measured level of physical resistance will achieve a desired performance level in the athletic activity, and to automatically generate control signals to adjust the level of physical resistance if the measured level of physical resistance is unlikely to achieve the desired performance level in the athletic activity.

The apparatus as claimed above wherein the sensor is a user-wearable air flow sensor.

The apparatus as claimed above wherein the controller is further configured to obtain a user profile for each of a plurality of participants engaged in the athletic activity and to compare the performance levels for each of the plurality of participants.

The apparatus as claimed above wherein the controller is further configured to adjust the level of physical resistance of a particular participant engaged in the athletic activity if the performance level of the particular participant does not substantially match the performance levels of a plurality of other participants engaged in the athletic activity.

The apparatus as claimed above wherein the controller is further configured to obtain a user profile for a particular participant engaged in the athletic activity and to compare the performance level of the particular participant in the athletic activity with a performance level of the particular participant in a prior athletic activity.

The apparatus as claimed above wherein the athletic activity is of a type from the group consisting of: bicycle riding, boating, and weight lifting.

The apparatus as claimed above wherein adjusting the level of physical resistance includes applying friction to a wheel of a bicycle.

The apparatus as claimed above wherein adjusting the level of physical resistance includes adjusting resistance rudders on a boat.

A method comprising: measuring a level of physical resistance in an athletic activity; generating sensor data indicative of the measured level of physical resistance; using the sensor data to determine if the measured level of physical resistance will achieve a desired performance level in the athletic activity; and automatically generating control signals to adjust the level of physical resistance if the measured level of physical resistance is unlikely to achieve the desired performance level in the athletic activity.

The method as claimed above wherein the sensor data is generated by a user-wearable air flow sensor.

The method as claimed above including obtaining a user profile for each of a plurality of participants engaged in the athletic activity and comparing the performance levels for each of the plurality of participants.

The method as claimed above including adjusting the level of physical resistance of a particular participant engaged in the athletic activity if the performance level of the particular participant does not substantially match the performance levels of a plurality of other participants engaged in the athletic activity.

The method as claimed above including obtaining a user profile for a particular participant engaged in the athletic activity and comparing the performance level of the particular participant in the athletic activity with a performance level of the particular participant in a prior athletic activity.

The method as claimed above wherein the athletic activity is of a type from the group consisting of: bicycle riding, boating, and weight lifting.

The method as claimed above wherein adjusting the level of physical resistance includes applying friction to a wheel of a bicycle.

The method as claimed above wherein adjusting the level of physical resistance includes adjusting resistance rudders on a boat.

A system comprising: a user-wearable air flow sensor to measure a level of physical resistance in an athletic activity and to generate sensor data indicative of the measured level of physical resistance; a controller to receive the sensor data, to determine if the measured level of physical resistance will achieve a desired performance level in the athletic activity, and to generate control signals to adjust the level of physical resistance if the measured level of physical resistance is unlikely to achieve the desired performance level in the athletic activity; and a bicycle equipped with a hybrid drive mechanism to enable automatic adjustment of the level of physical resistance applied to a wheel of the bicycle.

The system as claimed above wherein the sensor includes a wireless data transceiver.

The system as claimed above wherein the controller is further configured to obtain a user profile for each of a plurality of participants engaged in the athletic activity and to compare the performance levels for each of the plurality of participants.

The system as claimed above wherein the controller is further configured to adjust the level of physical resistance of a particular participant engaged in the athletic activity if the performance level of the particular participant does not substantially match the performance levels of a plurality of other participants engaged in the athletic activity.

The system as claimed above wherein the controller is further configured to obtain a user profile for a particular participant engaged in the athletic activity and to compare the performance level of the particular participant in the athletic activity with a performance level of the particular participant in a prior athletic activity.

The system as claimed above wherein adjusting the level of physical resistance includes automatically applying friction to the wheel of the bicycle.

The system as claimed above wherein adjusting the level of physical resistance includes automatically modifying the tire pressure of the wheel of the bicycle.

The system as claimed above wherein adjusting the level of physical resistance includes automatically applying a thrust force to the wheel of the bicycle.

An apparatus comprising: a sensing means to measure a level of physical resistance in an athletic activity and to generate sensor data indicative of the measured level of physical resistance; and a control means to receive the sensor data, to determine if the measured level of physical resistance will achieve a desired performance level in the athletic activity, and to automatically generate control signals to adjust the level of physical resistance if the measured level of physical resistance is unlikely to achieve the desired performance level in the athletic activity.

The apparatus as claimed above wherein the sensing means is a user-wearable air flow sensor.

The apparatus as claimed above wherein the control means is further configured to obtain a user profile for each of a plurality of participants engaged in the athletic activity and to compare the performance levels for each of the plurality of participants.

The apparatus as claimed above wherein the control means is further configured to adjust the level of physical resistance of a particular participant engaged in the athletic activity if the performance level of the particular participant does not substantially match the performance levels of a plurality of other participants engaged in the athletic activity.

The apparatus as claimed above wherein the control means is further configured to obtain a user profile for a particular participant engaged in the athletic activity and to compare the performance level of the particular participant in the athletic activity with a performance level of the particular participant in a prior athletic activity.

The apparatus as claimed above wherein the athletic activity is of a type from the group consisting of: bicycle riding, boating, and weight lifting.

The apparatus as claimed above wherein adjusting the level of physical resistance includes applying friction to a wheel of a bicycle.

The apparatus as claimed above wherein adjusting the level of physical resistance includes adjusting resistance rudders on a boat.

A non-transitory machine-useable storage medium embodying instructions which, when executed by a machine, cause the machine to: measure a level of physical resistance in an athletic activity; generate sensor data indicative of the measured level of physical resistance; use the sensor data to determine if the measured level of physical resistance will achieve a desired performance level in the athletic activity; and automatically generate control signals to adjust the level of physical resistance if the measured level of physical resistance is unlikely to achieve the desired performance level in the athletic activity.

The machine-useable storage medium as claimed above wherein the sensor data is generated by a user-wearable air flow sensor.

The machine-useable storage medium as claimed above being further configured to obtain a user profile for each of a plurality of participants engaged in the athletic activity and to compare the performance levels for each of the plurality of participants.

The machine-useable storage medium as claimed above being further configured to adjust the level of physical resistance of a particular participant engaged in the athletic activity if the performance level of the particular participant does not substantially match the performance levels of a plurality of other participants engaged in the athletic activity.

The machine-useable storage medium as claimed above being further configured to obtain a user profile for a particular participant engaged in the athletic activity and to compare the performance level of the particular participant in the athletic activity with a performance level of the particular participant in a prior athletic activity.

The machine-useable storage medium as claimed above wherein the athletic activity is of a type from the group consisting of: bicycle riding, boating, and weight lifting.

The machine-useable storage medium as claimed above wherein adjusting the level of physical resistance includes applying friction to a wheel of a bicycle.

The machine-useable storage medium as claimed above wherein adjusting the level of physical resistance includes adjusting resistance rudders on a boat.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A system comprising:
    a user-wearable sensor including a housing having a wearable form factor, the user-wearable sensor to measure a first level of physical effort during a first athletic activity using fitness equipment and to generate sensor data indicative of the first level of physical effort; and
    a controller to:
        determine a first force-to-motion ratio based on the sensor data;
        conduct effort normalization based on the first force-to-motion ratio and a second force-to-motion ratio based on data from a second athletic activity indicative of a second level of physical effort; and automatically generate a control signal to adjust a setting of the fitness equipment based on the effort normalization.

2. The system of claim 1, wherein the user-wearable sensor is to measure the first level of physical effort through a force adjacent the user.

3. The system of claim 2, wherein the force is air resistance.

4. The system of claim 2, wherein the force is a weight.

5. The system of claim 1, wherein the fitness equipment is first fitness equipment and the second athletic activity includes use of second fitness equipment different from the first equipment.

6. The system of claim 1, wherein the first athletic activity is at a first time and the second athletic activity includes use of the fitness equipment at a second time, the second time prior to the first time.

7. The system of claim 1, wherein the controller is to adjust the setting of the fitness equipment to decrease a physical resistance level when the effort normalization indicates a decrease level of physical effort.

8. The system of claim 1, wherein the user-wearable sensor is to measure the first level of physical effort through a physical signal generated by the user.

9. The system of claim 1, wherein the user-wearable sensor is to measure the first level of physical effort through a time of use of the fitness equipment.

10. The system of claim 1, wherein the controller is programmed to automatically generate the control signal to adjust a setting of the fitness equipment during use of the fitness equipment.

11. A system comprising:
a first user-wearable sensor including a first housing having a wearable form factor, the first user-wearable sensor to measure a physical signal generated by the user during a first athletic activity using fitness equipment;
a second user-wearable sensor including a second housing having a wearable form factor, the second user-wearable sensor to measure a force adjacent the user during the first athletic activity; and
a controller to:
determine a first level of physical effort exerted by the user based on the physical signal generated by the user and the force adjacent the user;
determine a first force-to-motion ratio based on the first level of physical effort;
determine a second force-to-motion ratio based on a second level of physical effort from a second athletic activity;
conduct effort normalization based on the first force-to-motion ratio and the second force-to-motion ratio; and
automatically generate a control signal to adjust a setting of the fitness equipment based on the effort normalization.

12. The system of claim 11, wherein the fitness equipment is first fitness equipment and the second athletic activity includes use of second fitness equipment different from the first equipment.

13. The system of claim 11, wherein the first athletic activity is at a first time and the second athletic activity includes use of the fitness equipment at a second time prior to the first time.

14. The system of claim 11, wherein the controller is to adjust the setting of the fitness equipment to decrease a physical resistance level when effort normalization indicates a decreased level of physical effort.

15. The system of claim 11, wherein the force is air resistance.

16. The system of claim 11, wherein the force is a weight.

17. The system of claim 11, wherein the controller is to automatically generate the control signal to adjust a setting of the fitness equipment during use of the fitness equipment.

18. A system comprising:
a user-wearable means for measuring a first level of physical effort during a first athletic activity using fitness equipment and generating sensor data indicative of the first level of physical effort, the user-wearable means including a housing having a wearable form factor;
means for processing the sensor data and data from a second athletic activity indicative of a second level of physical effort, the means for processing to:
determine a first force-to-motion ratio from the sensor data;
determine a second force-to-motion ratio from the data from the second athletic activity; and
conduct an effort normalization based on the first force-to-motion ratio and the second force-to-motion ratio; and
means for adjusting a setting of the fitness equipment based on the effort normalization.

* * * * *